(12) United States Patent
Boatman et al.

(10) Patent No.: US 9,358,141 B2
(45) Date of Patent: Jun. 7, 2016

(54) STENT DEPLOYMENT DEVICE

(75) Inventors: Scott E. Boatman, Bloomington, IN (US); Michael C. Hoffa, Brownsburg, IN (US); Kimberly D. Roberts, Bloomfield, IN (US); Darin G. Schaeffer, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1240 days.

(21) Appl. No.: 11/547,020

(22) PCT Filed: Mar. 22, 2005

(86) PCT No.: PCT/US2005/009376
§ 371 (c)(1),
(2), (4) Date: Jun. 7, 2007

(87) PCT Pub. No.: WO2005/099629
PCT Pub. Date: Oct. 27, 2005

(65) Prior Publication Data
US 2008/0046063 A1 Feb. 21, 2008

Related U.S. Application Data

(60) Provisional application No. 60/558,277, filed on Mar. 31, 2004.

(51) Int. Cl.
*A61F 2/958* (2013.01)
*A61F 2/82* (2013.01)

(52) U.S. Cl.
CPC ........... *A61F 2/958* (2013.01); *A61F 2002/821* (2013.01)

(58) Field of Classification Search
CPC .... A61F 2/954; A61F 2/958; A61F 2002/821

USPC ......................................................... 606/194
See application file for complete search history.

(56) References Cited

U.S. PATENT DOCUMENTS

| 4,562,596 A | 1/1986 | Kornberg ........................ 623/1 |
| 4,665,918 A | 5/1987 | Garza et al. ................... 128/343 |

(Continued)

FOREIGN PATENT DOCUMENTS

| EP | 0 461 791 A1 | 6/1991 | ................ A61F 2/06 |
| EP | 0 646 365 A1 | 9/1994 | ................ A61F 2/06 |

(Continued)

OTHER PUBLICATIONS

Tam Huynh, Ginger Abraham, James Murray, Kelvin Brockbank, Per-Otto Hagen, and Susan Sullivan; Remodeling of an acellular collagen graft into a physiologically responsive neovessel; Nature Biotechnology vol. 17 Nov. 1999.

(Continued)

*Primary Examiner* — Sarah W Aleman
(74) *Attorney, Agent, or Firm* — Brinks Gilson & Lione

(57) ABSTRACT

A stent deployment device (110) is provided for deploying a stent in a lumen of a patient. The device can include a catheter (112), a first balloon (122) positioned near a distal end of the catheter and a second balloon (123) adjacent to the first balloon. Alternatively, the second balloon can be positioned over the first balloon. The device also includes an expandable stent (210) positioned over the first balloon and the second balloon. The first balloon comprises a semi-compliant material, a non-compliant material or a compliant material. Similarly, the second balloon comprises a semi-compliant material, a non-compliant material or a compliant material. The first balloon is expandable to a first diameter, while the second balloon can be expandable to a second diameter.

20 Claims, 18 Drawing Sheets

(56) References Cited

U.S. PATENT DOCUMENTS

| | | | |
|---|---|---|---|
| 4,763,654 A * | 8/1988 | Jang | 606/195 |
| 4,902,508 A | 2/1990 | Badylak et al. | 424/95 |
| 4,950,227 A | 8/1990 | Savin et al. | 604/8 |
| 4,957,508 A | 9/1990 | Kaneko et al. | 623/12 |
| 5,071,406 A * | 12/1991 | Jang | 604/101.01 |
| 5,104,404 A | 4/1992 | Wolff | 623/1 |
| 5,123,917 A | 6/1992 | Lee | 623/1 |
| 5,320,605 A * | 6/1994 | Sahota | 604/101.01 |
| 5,387,235 A | 2/1995 | Chuter | 623/1 |
| 5,447,497 A | 9/1995 | Sogard et al. | 604/101 |
| 5,522,880 A | 6/1996 | Barone et al. | 623/1 |
| 5,556,383 A | 9/1996 | Wang et al. | 604/96 |
| 5,571,173 A | 11/1996 | Parodi | 623/1 |
| 5,578,071 A | 11/1996 | Parodi | 623/1 |
| 5,591,229 A | 1/1997 | Parodi | 623/1 |
| 5,607,444 A * | 3/1997 | Lam | 606/194 |
| 5,632,762 A * | 5/1997 | Myler | 606/194 |
| 5,653,743 A | 8/1997 | Martin | 623/1 |
| 5,693,084 A | 12/1997 | Chuter | 623/1 |
| 5,693,087 A | 12/1997 | Parodi | 623/1 |
| 5,711,969 A | 1/1998 | Patel et al. | 424/551 |
| 5,720,776 A | 2/1998 | Chuter et al. | 623/1 |
| 5,733,337 A | 3/1998 | Carr, Jr. et al. | 623/11 |
| 5,755,778 A | 5/1998 | Kleshinski | 623/1 |
| 5,851,228 A | 12/1998 | Pinheiro | 623/1 |
| 5,885,619 A | 3/1999 | Patel et al. | 424/551 |
| 5,921,995 A | 7/1999 | Kleshinski | 606/153 |
| 5,955,110 A | 9/1999 | Patel et al. | 424/551 |
| 5,957,974 A | 9/1999 | Thompson et al. | 623/1 |
| 5,961,548 A | 10/1999 | Shmulewitz | 623/1 |
| 5,968,096 A | 10/1999 | Whitson et al. | 623/15 |
| 5,984,955 A | 11/1999 | Wisselink | 623/1 |
| 6,010,530 A | 1/2000 | Goicoechea | 623/1 |
| 6,030,414 A | 2/2000 | Taheri | 623/1 |
| 6,053,941 A | 4/2000 | Lindenberg et al. | 623/1 |
| 6,056,700 A | 5/2000 | Burney et al. | 600/564 |
| 6,059,824 A | 5/2000 | Taheri | 623/1 |
| 6,074,416 A | 6/2000 | Berg et al. | 623/1 |
| 6,077,296 A | 6/2000 | Shokoohi et al. | 623/1 |
| 6,102,940 A | 8/2000 | Robichon et al. | 623/1 |
| 6,152,944 A | 11/2000 | Holman et al. | 606/194 |
| 6,152,956 A | 11/2000 | Pierce | 623/1.13 |
| 6,168,621 B1 | 1/2001 | Vrba | 623/1.2 |
| 6,171,329 B1 | 1/2001 | Shaw et al. | 606/213 |
| 6,176,875 B1 | 1/2001 | Lenker et al. | 623/1.49 |
| 6,187,033 B1 | 2/2001 | Schmitt | 623/1 |
| 6,206,931 B1 | 3/2001 | Cook et al. | 623/23.75 |
| 6,210,429 B1 | 4/2001 | Vardi et al. | 623/1.11 |
| 6,217,609 B1 | 4/2001 | Haverkost | 623/1.22 |
| 6,221,090 B1 | 4/2001 | Wilson | 606/194 |
| 6,238,430 B1 | 5/2001 | Klumb et al. | 623/1.11 |
| 6,290,728 B1 | 9/2001 | Phelps et al. | 623/23.7 |
| 6,290,731 B1 | 9/2001 | Solovay et al. | 623/51.16 |
| 6,325,819 B1 | 12/2001 | Pavenik et al. | 623/1.11 |
| 6,325,826 B1 | 12/2001 | Vardi et al. | 623/1.35 |
| 6,334,869 B1 | 1/2002 | Leonhardt et al. | 623/1.13 |
| 6,344,056 B1 | 2/2002 | Dehdashtian | 623/1.35 |
| 6,395,018 B1 | 5/2002 | Castaneda | 623/1.13 |
| 6,398,803 B1 | 6/2002 | Layne et al. | 623/1.13 |
| 6,409,756 B1 | 6/2002 | Murphy | 623/1.35 |
| 6,409,757 B1 | 6/2002 | Trout, III et al. | 623/1.36 |
| 6,428,565 B1 | 8/2002 | Wisselink | 623/1.11 |
| 6,447,540 B1 | 9/2002 | Fontaine et al. | 623/1.12 |
| 6,464,720 B2 | 10/2002 | Boatman et al. | 623/1.15 |
| 6,471,672 B1 | 10/2002 | Brown et al. | 604/101.01 |
| 6,482,227 B1 | 11/2002 | Solovay | 623/1.13 |
| 6,517,574 B1 | 2/2003 | Chuter | 623/1.23 |
| 6,520,988 B1 | 2/2003 | Colombo et al. | 623/1.35 |
| 6,524,335 B1 | 2/2003 | Hartley et al. | 623/1.15 |
| 6,527,799 B2 | 3/2003 | Shanley | 623/1.15 |
| 6,572,648 B1 | 6/2003 | Klumb et al. | 623/1.15 |
| 6,582,394 B1 | 6/2003 | Reiss et al. | 604/96.01 |
| 6,585,758 B1 | 7/2003 | Chouinard et al. | 623/1.16 |
| 6,616,675 B1 | 9/2003 | Evard et al. | 606/155 |
| 6,645,242 B1 | 11/2003 | Quinn | 623/1.16 |
| 6,652,567 B1 | 11/2003 | Deaton | 623/1.1 |
| 6,663,667 B2 | 12/2003 | Dehdashtian et al. | 623/1.51 |
| 6,669,720 B1 | 12/2003 | Pierce | 623/1.13 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,712,812 B2 | 3/2004 | Roschak et al. | 606/41 |
| 6,723,116 B2 | 4/2004 | Taheri | 623/1.13 |
| 6,733,522 B2 | 5/2004 | Schmitt et al. | 623/1.31 |
| 6,733,523 B2 | 5/2004 | Shaolian et al. | 623/1.35 |
| 6,761,734 B2 | 7/2004 | Suhr | 623/1.35 |
| 6,767,358 B2 | 7/2004 | Leonhardt et al. | 623/1.13 |
| 6,773,457 B2 | 8/2004 | Ivancev et al. | 623/1.28 |
| 6,814,752 B1 | 11/2004 | Chuter | 623/1.35 |
| 7,052,510 B1 * | 5/2006 | Richter | 623/1.11 |
| 2001/0027338 A1 | 10/2001 | Greenberg | 623/1.13 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0082684 A1 | 6/2002 | Mishaly | 623/1.36 |
| 2002/0099441 A1 | 7/2002 | Dehdashtian | 623/1.51 |
| 2002/0144696 A1 | 10/2002 | Sharkawy et al. | 128/898 |
| 2002/0156517 A1 | 10/2002 | Perouse | 623/1.11 |
| 2002/0156522 A1 | 10/2002 | Ivancev et al. | 623/1.13 |
| 2002/0193872 A1 | 12/2002 | Trout, III et al. | 623/1.34 |
| 2002/0198585 A1 | 12/2002 | Wisselink | 623/1.11 |
| 2003/0033005 A1 | 2/2003 | Houser et al. | 623/1.35 |
| 2003/0074050 A1 | 4/2003 | Kerr | 623/1.13 |
| 2003/0093145 A1 | 5/2003 | Lawrence-Brown et al. | 623/1.21 |
| 2003/0120333 A1 | 6/2003 | Ouriel et al. | 623/1.14 |
| 2003/0130720 A1 | 7/2003 | De Palma et al. | 623/1.13 |
| 2003/0130724 A1 | 7/2003 | De Palma et al. | 623/1.16 |
| 2003/0199967 A1 | 10/2003 | Hartley et al. | 623/1.13 |
| 2003/0199973 A1 | 10/2003 | Chuter et al. | 623/1.35 |
| 2003/0220682 A1 | 11/2003 | Kujawski | 623/1.13 |
| 2003/0225453 A1 | 12/2003 | Murch | 623/1.21 |
| 2003/0233140 A1 | 12/2003 | Hartley et al. | 623/1.11 |
| 2004/0024446 A1 | 2/2004 | Smith | 623/1.22 |
| 2004/0034406 A1 | 2/2004 | Thramann | 623/1.13 |
| 2004/0044396 A1 | 3/2004 | Clerc et al. | 623/1.13 |
| 2004/0054396 A1 | 3/2004 | Hartley et al. | 623/1.13 |
| 2004/0059406 A1 | 3/2004 | Cully et al. | 623/1.11 |
| 2004/0073288 A1 | 4/2004 | Kerr | 623/1.13 |
| 2004/0093078 A1 | 5/2004 | Moll et al. | 623/1.35 |
| 2004/0098079 A1 | 5/2004 | Hartley et al. | 623/1.11 |
| 2004/0106972 A1 | 6/2004 | Deaton | 623/1.1 |
| 2004/0117004 A1 | 6/2004 | Osborne et al. | 623/1.36 |
| 2004/0133266 A1 | 7/2004 | Clerc et al. | 623/1.22 |
| 2004/0138737 A1 | 7/2004 | Davidsons et al. | 623/1.35 |
| 2004/0167607 A1 | 8/2004 | Frantzen | 623/1.13 |
| 2004/0254627 A1 | 12/2004 | Thompson et al. | 623/1.11 |
| 2005/0049678 A1 | 3/2005 | Cocks et al. | 623/1.15 |
| 2005/0049680 A1 * | 3/2005 | Fischell et al. | 623/1.15 |
| 2005/0149166 A1 | 7/2005 | Schaeffer et al. | 623/1.13 |
| 2005/0171597 A1 | 8/2005 | Boatman et al. | 623/1.22 |
| 2005/0171598 A1 | 8/2005 | Schaeffer | 623/1.35 |
| 2005/0192656 A1 * | 9/2005 | Eidenschink | 623/1.11 |
| 2005/0222668 A1 | 10/2005 | Schaeffer et al. | 623/1.13 |
| 2006/0058864 A1 | 3/2006 | Schaeffer et al. | 623/1.11 |
| 2007/0179592 A1 | 8/2007 | Schaeffer | 623/1.35 |

FOREIGN PATENT DOCUMENTS

| | | | | |
|---|---|---|---|---|
| EP | 0 903 118 A2 | 9/1994 | | A61F 2/06 |
| JP | 404231954 A | 8/1992 | | |
| JP | 407008512 A | 1/1995 | | |
| WO | WO 98/22158 | 5/1998 | | A61L 27/00 |
| WO | WO 98/53761 | 12/1998 | | A61F 2/06 |
| WO | WO 99/36015 | 7/1999 | | A61F 11/00 |
| WO | WO 00/44307 | 8/2000 | | A61F 2/06 |
| WO | WO 02/067815 A1 | 9/2002 | | |
| WO | WO 03/020173 A1 | 3/2003 | | |
| WO | WO 03/034948 A1 | 5/2003 | | |
| WO | WO 03/053287 A1 | 7/2003 | | A61F 2/06 |

(56) References Cited

FOREIGN PATENT DOCUMENTS

WO     WO 03/065933 A1     8/2003
WO     WO 03/082153 A2     10/2003

OTHER PUBLICATIONS

International Search Report for PCT/US2004/037538 dated Apr. 4, 2005.
Office Action for U.S. Appl. No. 10/984,417 dated Nov. 16, 2006, 12 pages.
Amendment After Non-Final Rejection for U.S. Appl. No. 10/984,417 dated Feb. 13, 2007, 11 pages.
Office Action for U.S. Appl. No. 10/984,417 dated May 7, 2007, 14 pages.
Amendment After Final Rejection for U.S. Appl. No. 10/984,417 dated Aug. 10, 2007, 12 pages.
Office Action for U.S. Appl. No. 10/984,417 dated Oct. 10, 2007, 4 pages.
Request for Continued Examination and Response for U.S. Appl. No. 10/984,417 dated Oct. 23, 2007, 11 pages.
Office Action for U.S. Appl. No. 10/984,417 dated Jan. 8, 2008, 6 pages.
Response to Election/Restriction Requirement for U.S. Appl. No. 10/984,417 dated Jan. 31, 2008, 5 pages.
Office Action for U.S. Appl. No. 10/984,417 dated Feb. 26, 2008, 2 pages.
Response to Election/Restriction Requirement for U.S. Appl. No. 10/984,417 dated Mar. 7, 2008, 6 pages.
Office Action for U.S. Appl. No. 10/984,417 dated Jun. 26, 2008, 12 pages.
Amendment After Non-Final Rejection for U.S. Appl. No. 10/984,417 dated Sep. 26, 2008, 12 pages.
Office Action for U.S. Appl. No. 10/984,417 dated Oct. 20, 2008, 2 pages.
Amendment After Non-Final Rejection for U.S. Appl. No. 10/984,417 dated Nov. 3, 2008, 12 pages.
Office Action for U.S. Appl. No. 10/984,417 dated Jul. 29, 2009, 11 pages.
Office Action for U.S. Appl. No. 10/984,417 dated Nov. 20, 2009, 10 pages.
Office Action for U.S. Appl. No. 10/984,040 dated May 7, 2007, 8 pages.
Amendment After Non-Final Action for U.S. Appl. No. 10/984,040 dated Sep. 6, 2007, 8 pages.
Office Action for U.S. Appl. No. 10/984,040 dated Nov. 16, 2007, 5 pages.
Amendment After Non-Final Action for U.S. Appl. No. 10/984,040 dated Feb. 18, 2008, 9 pages.
Office Action for U.S. Appl. No. 10/984,040 dated May 1, 2008, 9 pages.
Request for Continued Examination and Amendment for U.S. Appl. No. 10/984,040 dated Sep. 30, 2008, 14 pages.
Office Action for U.S. Appl. No. 10/984,040 dated Oct. 30, 2008, 6 pages.
Applicant Summary of Interview for U.S. Appl. No. 10/984,040 dated Feb. 25, 2009, 2 pages.
Restriction Requirement for U.S. Appl. No. 10/984,040 dated Apr. 28, 2009, 9 pages.
Response to Restriction Requirement for U.S. Appl. No. 10/984,040 dated May 21, 2009, 7 pages.
Restriction Requirement for U.S. Appl. No. 10/984,040 dated Aug. 3, 2009, 6 pages.
Office Action for U.S. Appl. No. 10/984,416 dated Feb. 20, 2008, 14 pages.
Amendment After Non-Final Rejection for U.S. Appl. No. 10/984,416 dated May 20, 2008, 10 pages.
Office Action for U.S. Appl. No. 10/984,416 dated Aug. 18, 2008, 8 pages.
Request for Continued Examination and Amendment for U.S. Appl. No. 10/984,416 dated Oct. 13, 2008, 13 pages.
Office Action for U.S. Appl. No. 10/984,416 dated Nov. 26, 2008, 10 pages.
Amendment After Non-Final Action for U.S. Appl. No. 10/984,416 dated Mar. 26, 2009, 10 pages.
Office Action for U.S. Appl. No. 10/984,416 dated Jul. 9, 2009, 13 pages.
Request for Continued Examination and Amendment for U.S. Appl. No. 10/984,416 dated Oct. 15, 2009, 12 pages.
Office Action for U.S. Appl. No. 10/984,167 dated Nov. 16, 2006, 13 pages.
Amendment After Non-Final Action for U.S. Appl. No. 10/984,167 dated Feb. 15, 2007, 11 pages.
Office Action for U.S. Appl. No. 10/984,167 dated Apr. 27, 2007, 11 pages.
Amendment After Final Rejection for U.S. Appl. No. 10/984,167 dated Aug. 27, 2007, 9 pages.
Advisory Action for U.S. Appl. No. 10/984,167 dated Sep. 18, 2007, 3 pages.
Request for Continued Examination and Amendment for U.S. Appl. No. 10/984,167 dated Sep. 27, 2007, 10 pages.
Office Action for U.S. Appl. No. 10/984,167 dated Oct. 30, 2007, 10 pages.
Amendment After Non-Final Action for U.S. Appl. No. 10/984,167 dated Jan. 28, 2008, 9 pages.
Office Action for U.S. Appl. No. 10/984,167 dated Apr. 22, 2008, 11 pages.
Request for Continued Examination and Amendment for U.S. Appl. No. 10/984,167 dated Sep. 22, 2008, 11 pages.
Office Action for U.S. Appl. No. 10/984,167 dated Nov. 28, 2008, 10 pages.
Amendment after Non-Final Action for U.S. Appl. No. 10/984,167 dated Mar. 30, 2009, 13 pages.
Office Action for U.S. Appl. No. 10/984,167 dated Jun. 1, 2009, 11 pages.
Amendment After Final Action for U.S. Appl. No. 10/984,167 dated Aug. 3, 2009, 8 pages.
Advisory Action for U.S. Appl. No. 10/984,167 dated Aug. 13, 2009, 3 pages.
Notice of Appeal for U.S. Appl. No. 10/984,167 dated Sep. 1, 2009, 1 page.
Request for Pre-Appeal Review for U.S. Appl. No. 10/984,167 dated Sep. 1, 2009, 6 pages.
Pre-Appeal Panel Decision for U.S. Appl. No. 10/984,167 dated Nov. 24, 2009, 2 pgs.
Office Action for U.S. Appl. No. 10/984,131 dated Nov. 16, 2006, 12 pages.
Amendment After Non-Final Rejection for U.S. Appl. No. 10/984,131 dated Mar. 16, 2007, 10 pages.
Office Action for U.S. Appl. No. 10/984,131 dated Jun. 22, 2007, 12 pages.
Amendment After Final Rejection for U.S. Appl. No. 10/984,131 dated Aug. 22, 2007, 11 pages.
Advisory Action for U.S. Appl. No. 10/984,131 dated Sep. 18, 2007, 3 pages.
Request for Continued Examination and Amendment for U.S. Appl. No. 10/984,131 dated Sep. 28, 2007, 11 pages.
Office Action for U.S. Appl. No. 10/984,131 dated Dec. 12, 2007, 13 pages.
Amendment After Non-Final Action for U.S. Appl. No. 10/984,131 dated Apr. 14, 2008, 10 pages.
Office Action for U.S. Appl. No. 10/984,131 dated Aug. 14, 2008, 14 pages.
Request for Continued Examination and Amendment for U.S. Appl. No. 10/984,131 dated Oct. 13, 2008, 14 pages.
Office Action for U.S. Appl. No. 10/984,131 dated Jan. 5, 2009, 10 pages.
Amendment After Non-Final Action for U.S. Appl. No. 10/984,131 dated May 5, 2009, 10 pages.
Office Action for U.S. Appl. No. 10/984,131 dated Jul. 24, 2009, 12 pages.
Amendment After Final Rejection for U.S. Appl. No. 10/984,131 dated Sep. 24, 2009, 10 pages.

(56) References Cited

OTHER PUBLICATIONS

Advisory Action for U.S. Appl. No. 10/984,131 dated Oct. 5, 2009, 3 pages.
Notice of Appeal for U.S. Appl. No. 10/984,131 dated Oct. 26, 2009, 1 page.
Request for Pre-Appeal Review for U.S. Appl. No. 10/984,131 dated Oct. 26, 2009, 6 pages.
Pre-Appeal Panel Decision for U.S. Appl. No. 10/984,131 dated Dec. 23, 2009, 2 pages.
Office Action for U.S. Appl. No. 10/984,520 dated Nov. 27, 2006, 16 pages.
Amendment After Non-Final Rejection for U.S. Appl. No. 10/984,520 dated Feb. 27, 2007, 16 pages.
Office Action for U.S. Appl. No. 10/984,520 dated May 15, 2007, 10 pages.
Amendment After Final Rejection for U.S. Appl. No. 10/984,520 dated Aug. 15, 2007, 8 pages.
Advisory Action for U.S. Appl. No. 10/984,520 dated Sep. 6, 2007, 3 pages.
Request for Continued Examination and Amendment for U.S. Appl. No. 10/984,520 dated Oct. 15, 2007, 9 pages.
Office Action for U.S. Appl. No. 10/984,520 dated Dec. 28, 2007, 8 pages.
Amendment After Non-Final Rejection for U.S. Appl. No. 10/984,520 dated Mar. 28, 2008, 8 pages.
Office Action for U.S. Appl. No. 10/984,520 dated Jun. 23, 2008, 9 pages.
Request for Continued Examination and Amendment for U.S. Appl. No. 10/984,520 dated Sep. 22, 2008, 14 pages.
Office Action for U.S. Appl. No. 10/984,520 dated Dec. 9, 2008, 8 pages.
Amendment After Non-Final Rejection for U.S. Appl. No. 10/984,520 dated May 11, 2009, 9 pages.
Office Action for U.S. Appl. No. 10/984,520 dated Aug. 17, 2009, 10 pages.
European Patent Office Summons to Attend Oral Proceedings issued Feb. 18, 2010, in European Patent Application No. 05725997.0, 4 pgs.
European Patent Office Result of Consultation issued Jun. 8, 2010, in European Patent Application No. 05725997.0, 3 pgs.

\* cited by examiner

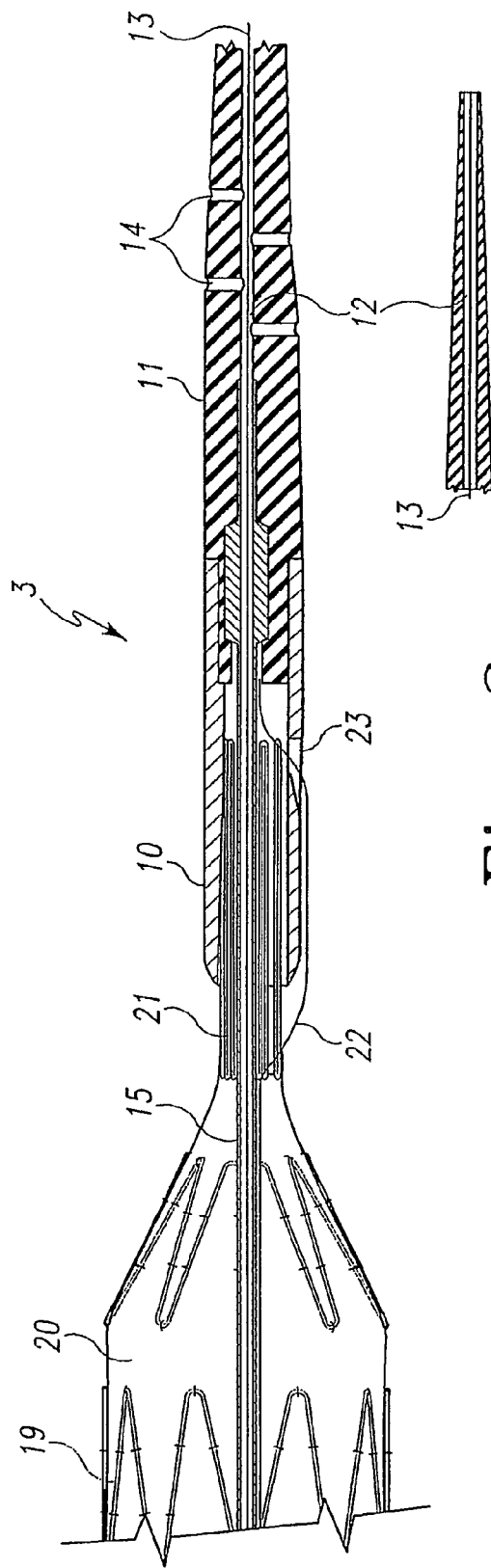
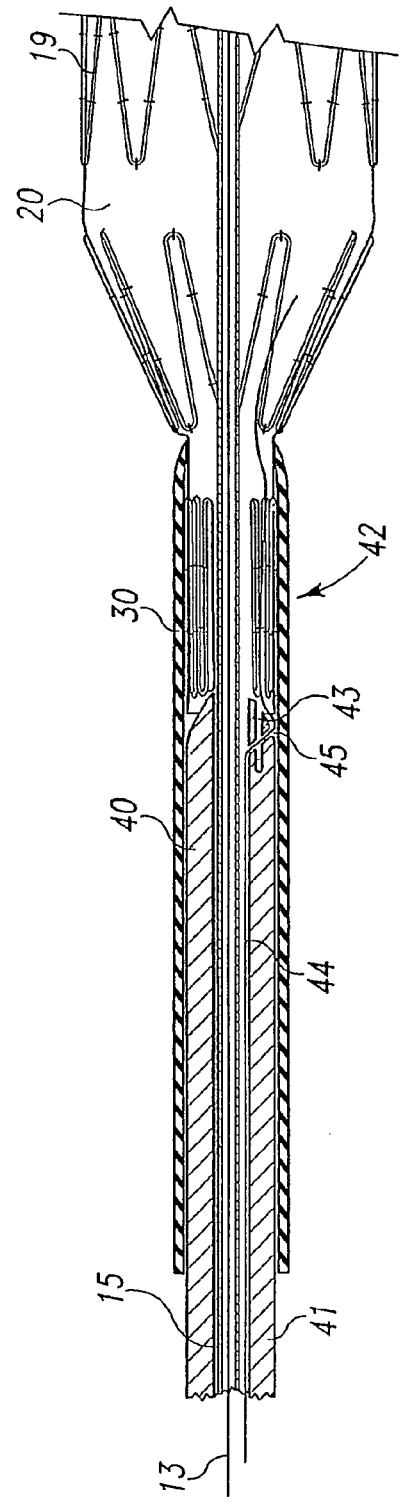
Fig. 2
Fig. 3

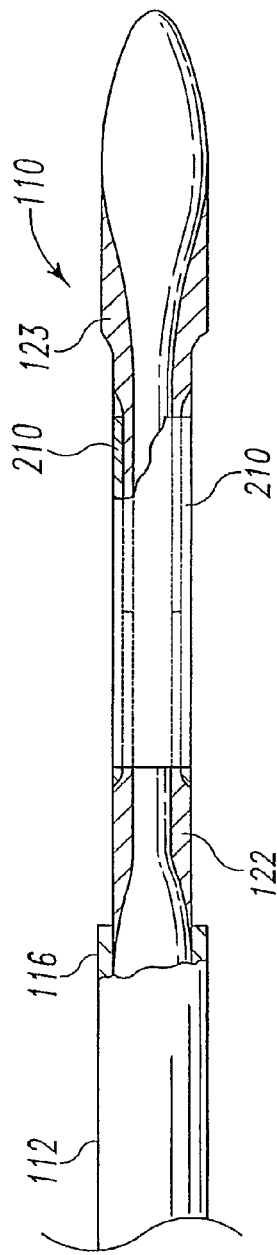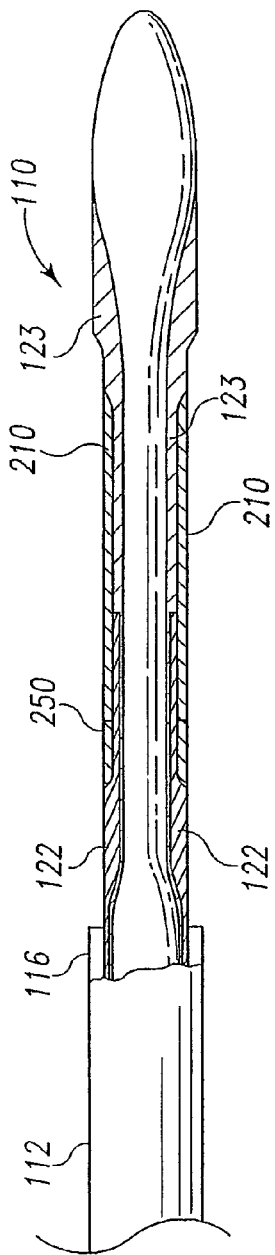
Fig. 16
Fig. 17

STENT DEPLOYMENT DEVICE

CROSS-REFERENCE TO RELATED APPLICATIONS

This application is related to and claims all benefits from PCT/US2005/0093756 filed Mar. 22, 2005, which is in turn based on U.S. Provisional Application 60/558,227 filed Mar. 31, 2004, both of which are hereby incorporated by reference.

BACKGROUND OF THE INVENTION

1. Technical Field

This invention relates to a medical device and, in particular, a prosthesis for implantation within the human or animal body for the repair of damaged vessels such as blood vessels.

2. Related Art

Throughout this specification, when discussing the aorta or other blood vessels, the terms distal and distally with respect to devices such as a prosthesis and a deployment system for a prosthesis are intended to refer to the end of the device furthest away from an operator during use of the device, or that is initially inserted into a patient or nearest the patient. Similarly, the terms proximal and proximally are intended to mean the end of the device nearest to the operator during use of the device.

The functional vessels of humans, such as blood vessels and ducts, occasionally weaken or even rupture. For example, the aortic wall can weaken, resulting in an aneurysm. Upon further exposure to haemodynamic forces, such an aneurysm can rupture. A common surgical intervention for weakened, aneurismal or ruptured vessels is the use of a prosthesis to provide some or all of the functionality of the original, healthy vessel and/or preserve any remaining vascular integrity by replacing a length of the existing vessel wall that spans the site of vessel failure.

The deployment of intraluminal prostheses into the lumen of a patient from a remote location by the use of a deployment device or introducer has been disclosed in a number of earlier patents and patent applications. U.S. Pat. No. 4,562,596 entitled "Aortic Graft, Device and Method for Performing an Intraluminal Abdominal Aortic Aneurysm Repair" proposes the retention of a self expanding graft within a sleeve until it is to be deployed, at which time the sleeve is withdrawn and the graft is allowed to expand. These features and other features disclosed in U.S. Pat. No. 4,562,596 could be used with the present invention and the disclosure of U.S. Pat. No. 4,562,596 is herein incorporated by reference.

U.S. Pat. No. 4,665,918 entitled "Prosthesis System and Method" proposes a system and method for the deployment of a prosthesis in a blood vessel. The prosthesis is positioned between a delivery catheter and an outer sheath and expands outwardly upon removal of the sheath. These features and other features disclosed in U.S. Pat. No. 4,665,918 could be used with the present invention and the disclosure of U.S. Pat. No. 4,665,918 is herein incorporated by reference.

U.S. Pat. No. 4,950,227 entitled "Stent Delivery System" proposes the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stent released and expanded into position. These features and other features disclosed in U.S. Pat. No. 4,950,227 could be used with the present invention and the disclosure of U.S. Pat. No. 4,950,227 is herein incorporated by reference.

U.S. Pat. No. 5,387,235 entitled "Expandable Transluminal Graft Prosthesis for Repair of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herein incorporated by reference.

U.S. Pat. No. 5,720,776 entitled "Barb and Expandable Transluminal Graft Prosthesis for Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herein incorporated by reference.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herein incorporated by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention and the disclosure of PCT Patent Publication Number No. WO99/29262 is herein incorporated by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention and the disclosure of PCT Patent Publication Number No. WO03/034948 is herein incorporated by reference.

United States Patent Application Publication No. 2003/0233140 A1 entitled "Trigger Wire System" discloses release wire systems for the release of stent grafts retained on introducer devices. This feature and other features disclosed in United States Patent Application Publication No. 2003/0233140 A1 could be used with the present invention and the disclosure of United States Patent Application Publication No. 2003/0233140 A1 is herein incorporated by reference.

United States Patent Application Publication No. 2004/0098079 A1 entitled "Thoracic Aortic Stent Graft Deployment Device" discloses introducer devices adapted for deployment of stent grafts particularly in the thoracic arch. This feature and other features disclosed in United States Patent Application Publication No. 2004/0098079 A1 could be used with the present invention and the disclosure of United States Patent Application Publication No. 2004/0098079 A1 is herein incorporated by reference.

United States Patent Application Publication No. 2004/0054396 A1 entitled "Stent-Graft Fastening" discloses arrangements for fastening stents onto grafts particularly for exposed stents. This feature and other features disclosed in United States Patent Application Publication No. 2004/0054396 A1 could be used with the present invention and the disclosure of United States Patent Application Publication No. 2004/0054396 A1 is herein incorporated by reference.

PCT Patent Publication Number No. WO03/053287 entitled "Stent Graft with Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention and the disclosure of PCT Patent Publication Number No. WO03/053287 is herein incorporated by reference.

PCT Patent Publication Number No. WO98/53761 entitled "A Prosthesis and a Method and Means of Deploying a Prosthesis" discloses various embodiments of an introducer for positioning an expandable, endovascular prosthesis in a lumen of a patient. This feature and other features disclosed in PCT Patent Publication Number No. WO98/53761 could be used with the present invention and the disclosure of PCT Patent Publication Number No. WO98/53761 is herein incorporated by reference.

One issue that arises with the use of an endoluminal prosthesis is where the damage in a vessel is at or near a branching vessel. For example, an abdominal aortic aneurysm may exist near the renal arteries, and a thoracic aortic aneurysm may exist near the left subclavian, common carotid, and/or innominate arteries. It would be desirable to prevent the prostheses from obstructing a branch vessel. It may also be desirable to include a fenestration in a wall of an intraluminal prosthesis to allow fluid communication between the interior cavity of the prosthesis and a branch vessel adjacent to the prostheses. It may be further desirable to maintain an alignment between such a fenestration and an opening to a branch vessel.

SUMMARY

A stent deployment device is provided. The device can include a catheter, a first balloon positioned near a distal end of the catheter and a second balloon adjacent to the first balloon. Alternatively, the second balloon can be positioned over the first balloon. The device also includes an expandable stent positioned over the first balloon and over the second balloon. The first balloon comprises a semi-compliant material, a noncompliant material or a compliant material. Similarly, the second balloon comprises a semi-compliant material, a noncompliant material or a compliant material. The first balloon is expandable to first diameter, while the second balloon is expandable to a second diameter.

The expandable stent can comprise an elongated member with a passage extending longitudinally therethrough. The expandable stent can also comprise a plurality of bendable tabs located at a longitudinal end of the expandable stent. The plurality of bendable tabs is positioned over the second balloon. Each of the bendable tabs can be configured to bend substantially radially outwardly from a body of the expandable stent. The expandable stent can further comprise one or more radio opaque markers positioned on a body of the expandable stent near one or more of the bendable tabs.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 2 is a sectional detail view of a portion of the introducer of FIG. 1A around the proximal end of the prosthesis.

FIG. 3 is a sectional detail view of a portion of the introducer of FIG. 1A around the distal end of the prosthesis.

FIG. 16 is a view similar to FIG. 15 with a sleeve of the introducer pulled back to expose a stent.

FIG. 17 is a detailed cross-sectional view of a portion of the endovascular introducer of FIG. 14.

DETAILED DESCRIPTION OF THE PREFERRED EMBODIMENTS

Figures 1A, 1B:
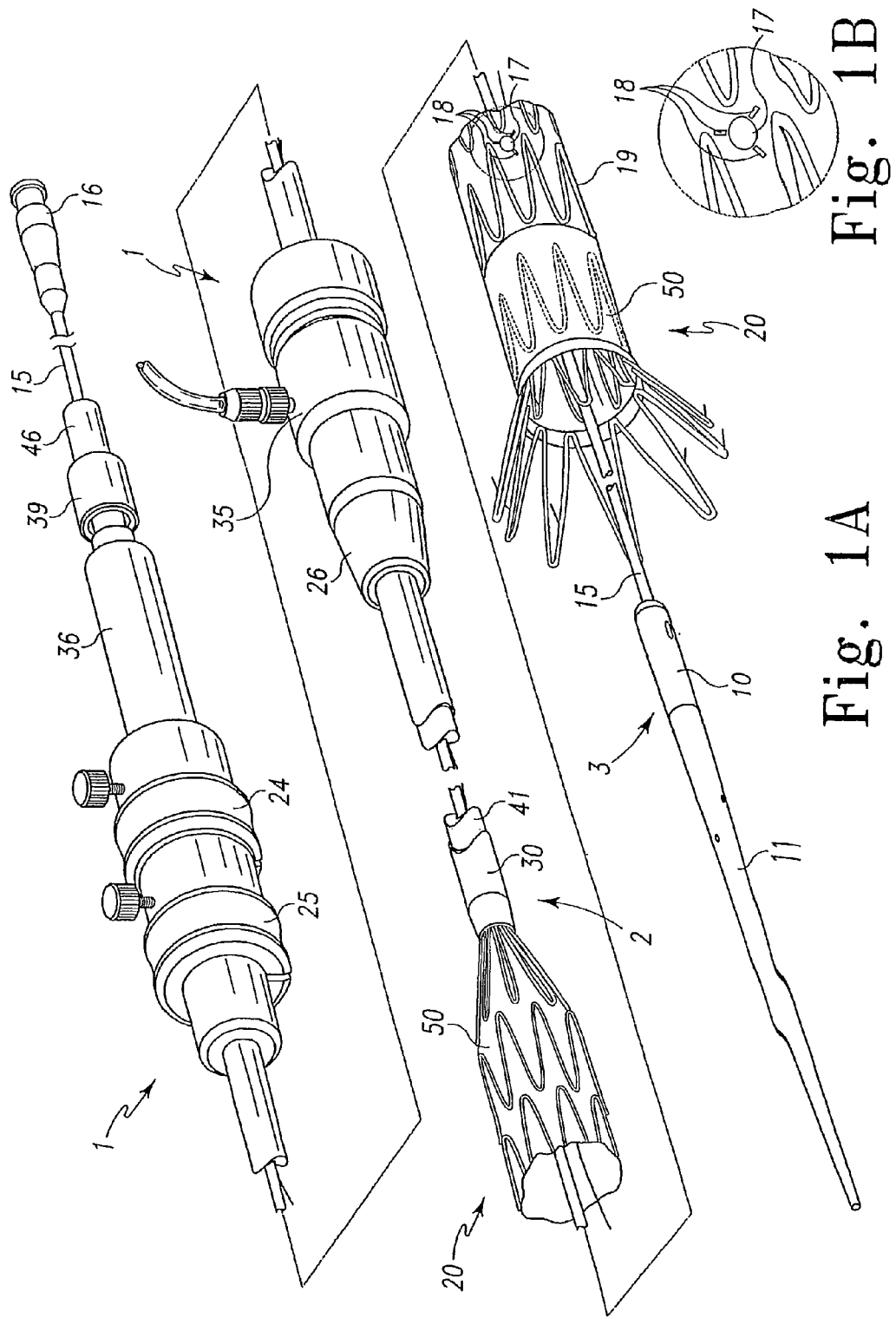
FIG. 1A is an exploded perspective view of an introducer with a first prosthesis partially deployed.
FIG. 1B is a close-up detail view of a portion of FIG. 1A.

FIG. 1A shows an endoluminal prosthesis 20, and an endovascular deployment system, also known as an introducer, for deploying the prosthesis 20 in a lumen of a patient during a medical procedure. The term "prosthesis" means any replacement for a body part or function of that body part. It can also mean a device that enhances or adds functionality to a physiological system. The terms "endoluminal" and "intraluminal" describe objects that are found or can be placed inside a lumen in the human or animal body. A lumen can be an existing lumens or a lumen created by surgical intervention. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The introducer includes an external manipulation section 1, a distal positioning mechanism and attachment region 2 and a proximal positioning mechanism attachment region 3. During a medical procedure to deploy the prosthesis 20, the distal and proximal attachment regions 2 and 3 will travel through the lumen to a desired deployment site. The external manipulation section 1, which is acted upon by a user to manipulate the introducer, remains outside of the patient throughout the procedure.

The prosthesis 20 comprises a tubular graft material 50, with self expanding stents 19 attached thereto. The term "graft" means the generally cannular or tubular member which acts as an artificial vessel. A graft by itself or with the addition of other elements can be an endoluminal prosthesis. The term "stent" means any device or structure that adds rigidity, expansion force or support to a prosthesis.

The tubular graft material 50 is preferably non-porous so that it does not leak or sweat under physiologic forces. The graft material is preferably made of woven DACRON® polyester (VASCUTEK® Ltd., Renfrewshire, Scotland, UK). The tubular graft can be made of any other at least substantially biocompatible material including such materials as other polyester fabrics, polytetrafluoroethylene (PTFE), expanded PTFE, and other synthetic materials known to those of skill in the art. Naturally occurring biomaterials, such as collagen, are also highly desirable, particularly a derived collagen material known as extracellular matrix (ECM), such as small intestinal submucosa (SIS).

Other examples of ECMs are pericardium, stomach submucosa, liver basement membrane, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr, Jr.; 17 Nature Biotechnology 1083 (November 1999); and WIPO Publication WO 98/22158 of May 28, 1998, to Cook et al., which is the published application of PCT/U.S.97/14855. All of these patents and publications are incorporated herein by reference.

Irrespective of the origin of the graft material (synthetic versus naturally occurring), the graft material can be made thicker by making multi-laminate constructs, for example SIS constructs as described in U.S. Pat. Nos. 5,968,096; 5,955, 110; 5,885,619; and 5,711,969. All of these patents are incorporated herein by reference. In addition to xenogenic biomaterials, such as SIS, autologous tissue can be harvested as well, for use in forming the graft material. Additionally elastin or elastin-like polypeptides (ELPs) and the like offer potential as a material to fabricate the graft material.

The self expanding stents 19 cause the prosthesis 20 to expand following its disengagement from the introducer. The prosthesis 20 also includes a self expanding zigzag stent 21 that extends from its proximal end. When it is disengaged, the self expanding zigzag stent 21 anchors the proximal end of the prosthesis 20 to the lumen.

One or more fenestrations 17 can be provided in the tubular graft material 50. Radiographic markers 18 can be attached to the tubular graft material 50 adjacent to the fenestration 17 in order to aid alignment of the fenestration 17 with a branch vessel. For example, the radiographic markers 18 can be small rings of metal, such as stainless steel, sewn to the tubular graft material 50 with suture.

FIG. 2 shows the proximal attachment region 3 in greater detail. The proximal attachment region 3 includes a cylindrical sleeve 10. The cylindrical sleeve 10 has a long tapered flexible extension 11 extending from its proximal end. The flexible extension 11 has an internal longitudinal aperture 12. The longitudinal aperture 12 facilitates advancement of the tapered flexible extension 11 along an insertion wire 13. The aperture 12 also provides a channel for the introduction of medical reagents, which will flow through openings 14. For example, it may be desirable to supply a contrast agent to allow angiography to be performed during placement and deployment phases of the medical procedure.

A thin walled tube 15 is fastened to the extension 11. The thin walled tube 15 can be made of metal but is still sufficiently flexible so that the introducer can be advanced along a relatively tortuous vessel, such as a femoral artery, and also to allow manipulation longitudinally and rotationally of the proximal attachment region 3. The thin walled tube 15 extends through the introducer to the manipulation section 1, terminating at a connection means 16, as shown in FIG. 6.

Figure 6:
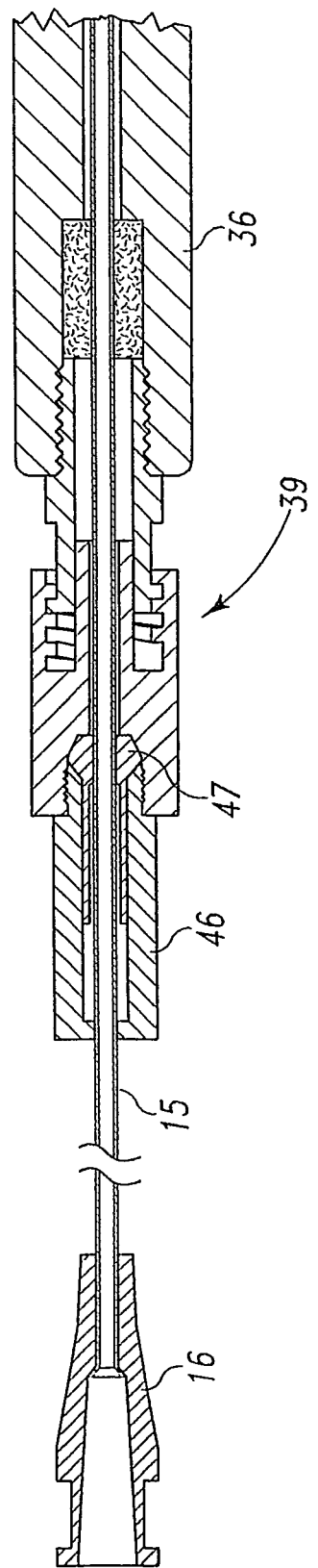
FIG. 6 is a sectional detail view of a portion of the introducer of FIG. 1A around the pin vise clamp and the medical reagent introduction tube.

Regarding the introduction of reagents, FIG. 6 also shows that the connection means 16 is adapted to accept a syringe to facilitate the introduction of reagents into the tube 15. The tube 15 is in fluid communication with the longitudinal aperture 12 of the flexible extension 11. Therefore, reagents can be introduced into the connection means 16 to flow through the longitudinal aperture 12 and emanate from the openings 14.

Figure 5:
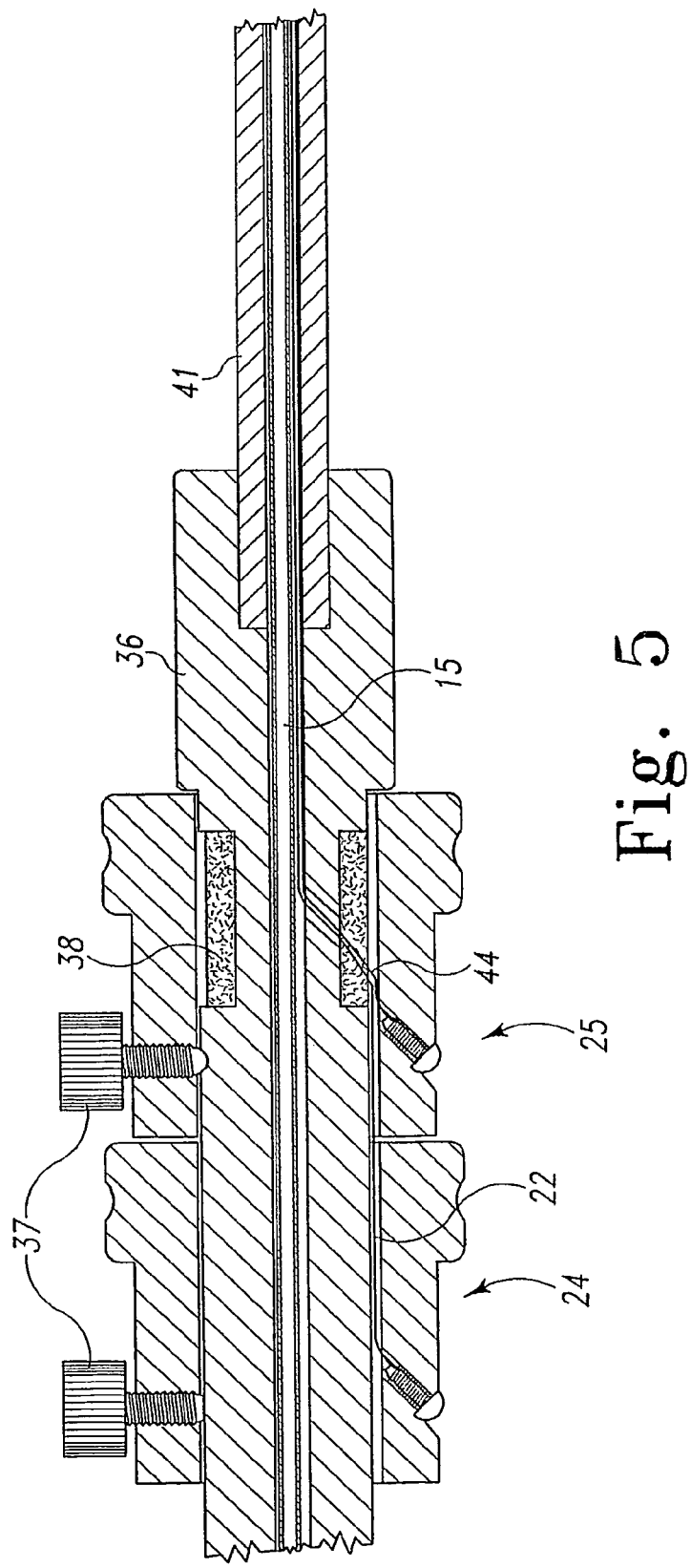
FIG. 5 is a sectional detail view of a portion of the introducer of FIG. 1A around the trigger wire release mechanisms.

As shown in FIG. 3, a tube 41 which can be made of plastic is coaxial with and radially outside the thin walled tube 15. The tube 41 is "thick walled", that is to say the thickness of its wall is several times that of the thin walled tube 15. A sheath 30 is coaxial with and radially outside the thick walled tube 41. The thick walled tube 41 and the sheath 30 extend distally to the manipulation region 1, as shown in FIG. 5.

FIGS. 2 and 3 illustrate retention, and distal and proximal release, mechanisms of the introducer, respectively. During the placement phase of a medical procedure, the prosthesis 20 is retained in a compressed condition by the sheath 30. The sheath 30 extends distally to a gripping and haemostatic sealing means 35 of the external manipulation section 1, shown in FIG. 4.

During assembly of the introducer, the sheath 30 is advanced over the cylindrical sleeve 10 of the proximal attachment region 3 while the prosthesis 20 is held in a compressed state by an external force. A distal attachment (retention) section 40 is formed in the thick walled tube 41 to retain the distal end of the prosthesis 20. Alternatively, the distal attachment section 40 can be a separate piece coupled to the thick walled tube 41.

The self-expanding stent 21 is released by retracting the sheath 30, removing the trigger wire 22, and then sliding the proximal attachment region 3, including the retention device 10, proximally away from the stent 21. Once the retention device 10 has cleared the self-expanding stent 21, the stent 21 will expand. The trigger wire 22 and the proximal wire release mechanism 24 form a control member to selectively release the retention device 10 from the prosthesis 20 by holding the self-expanding stent 21 in the retention device 10 until the prosthesis 20 is positioned at a desired site in a lumen.

The distal end 42 of the prosthesis 20 is retained by the distal attachment section 40 of the thick walled tube 41. The distal end 42 of the prosthesis 20 has a loop 43 through which a distal trigger wire 44 extends. The distal trigger wire 44 extends through an aperture 45 in the distal attachment section 40 into the annular region between the thin walled tube 15 and the thick walled tube 41.

As shown in FIG. 5, the distal trigger wire 44 extends through the annular space between the thick walled tube 41 and the thin walled tube 15 to the manipulation region 1. The distal trigger wire 44 exits the annular space at a distal wire release mechanism 25. The distal trigger wire 44 and the distal wire release mechanism 25 form a control member to selectively disengage the distal retention section 40 from the prosthesis 20 when it is positioned at a desired site in a lumen.

Figure 4:
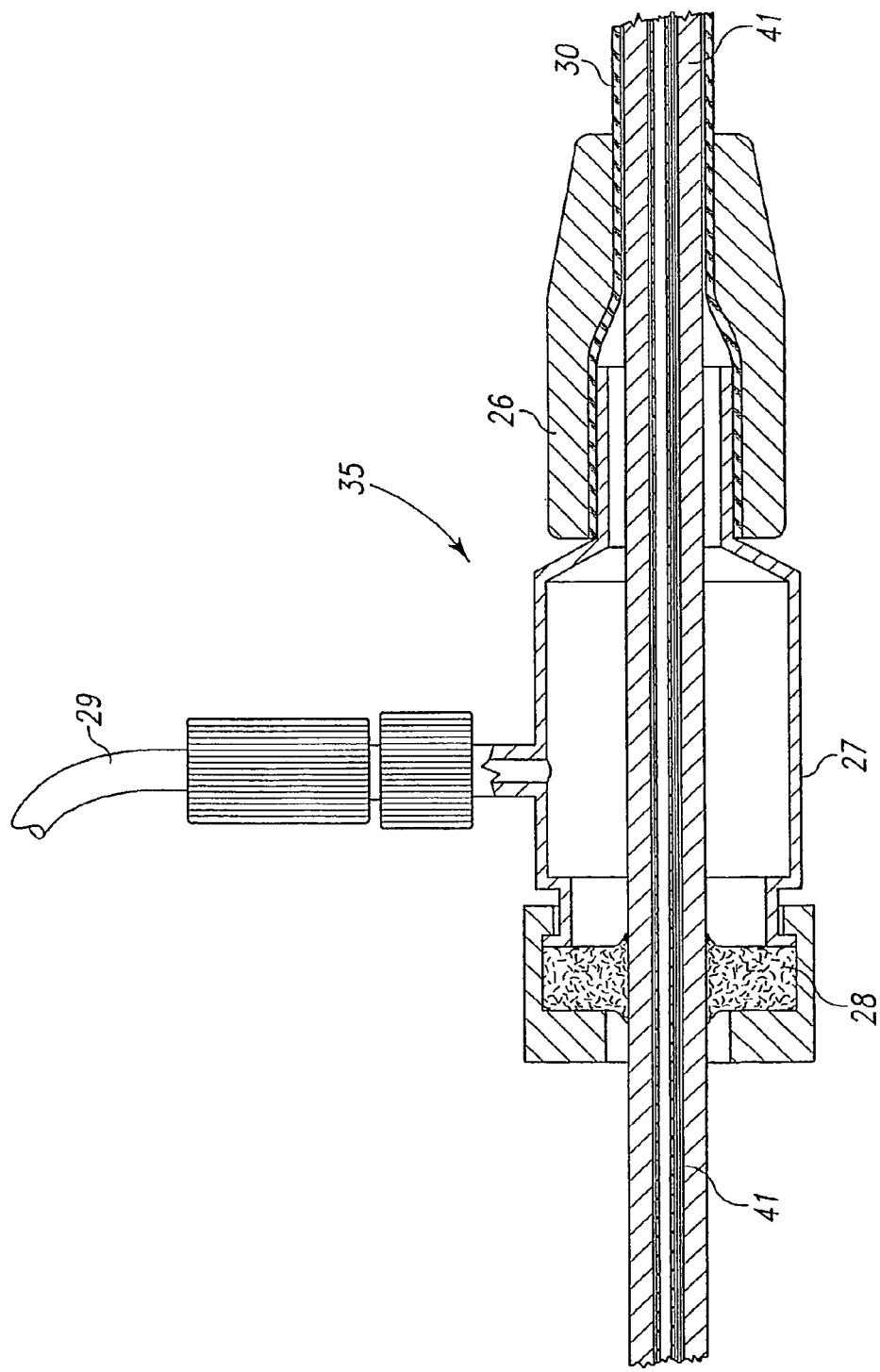
FIG. 4 is a sectional detail view of a portion of the introducer of FIG. 1A around the haemostatic seal.

FIG. 4 shows the haemostatic sealing means 35 of the external manipulation section 1 in greater detail. The haemostatic sealing means 35 includes a haemostatic seal 27 and a side tube 29. The haemostatic seal 27 includes a clamping collar 26 that clamps the sheath 30 to the haemostatic seal 27. The haemostatic seal 27 also includes a seal ring 28. The seal ring 28 can be formed of expanded silicone as a haemostatic seal around the thick walled tube 41. The side tube 29 facilitates the introduction of medical reagents between the thick walled tube 41 and the sheath 30.

FIG. 5 shows a proximal portion of the external manipulation section 1. The release wire actuation section has a body 36 that is mounted onto the thick walled plastic tube 41. The thin walled tube 15 passes through the body 36. The distal wire release mechanism 25 is mounted for slidable movement on the body 36. Similarly, the proximal wire release mechanism 22 is mounted for slidable movement on the body 36. A pair of clamping screws 37 prevents inadvertent early release of the prosthesis 20.

The positioning of the proximal and distal wire release mechanisms 24 and 25 is such that the proximal wire release mechanism 24 must be moved before the distal wire release mechanism 25 can be moved. Therefore, the distal end 42 of the prosthesis 20 cannot be released until the self-expanding zigzag stent 21 has been released and anchored to the lumen. A haemostatic seal 38 is provided so the release wires 22 and 44 can extend out through the body 36 to the release mechanisms 24 and 25 without unnecessary blood loss during the medical procedure.

FIG. 6 shows a distal portion of the external manipulation section 1. A pin vise 39 is mounted onto the distal end of the body 36. The pin vise 39 has a screw cap 46. When screwed in, the vise jaws 47 clamp against and engage the thin walled tube 15. When the vise jaws 47 are engaged, the thin walled tube 15 can only move with the body 36, and hence the thin walled tube 15 can only move with the thick walled tube 41. With the screw cap 46 tightened, the entire assembly, except for the external sleeve 30, can be moved as one.

The prosthesis 20 can be deployed in any method known in the art, preferably the method described in WO98/53761 in which the device is inserted by an introducer via a surgical cut-down into a femoral artery, and then advanced into the desired position over a stiff wire guide using endoluminal interventional techniques. For example, FIGS. 7 through 12 show various stages of the deployment of the prosthesis 20 during an illustrative medical procedure. A guide wire 13 is introduced into the femoral artery and advanced until its tip is beyond the region into which the prosthesis 20 is to be deployed.

Figure 7:
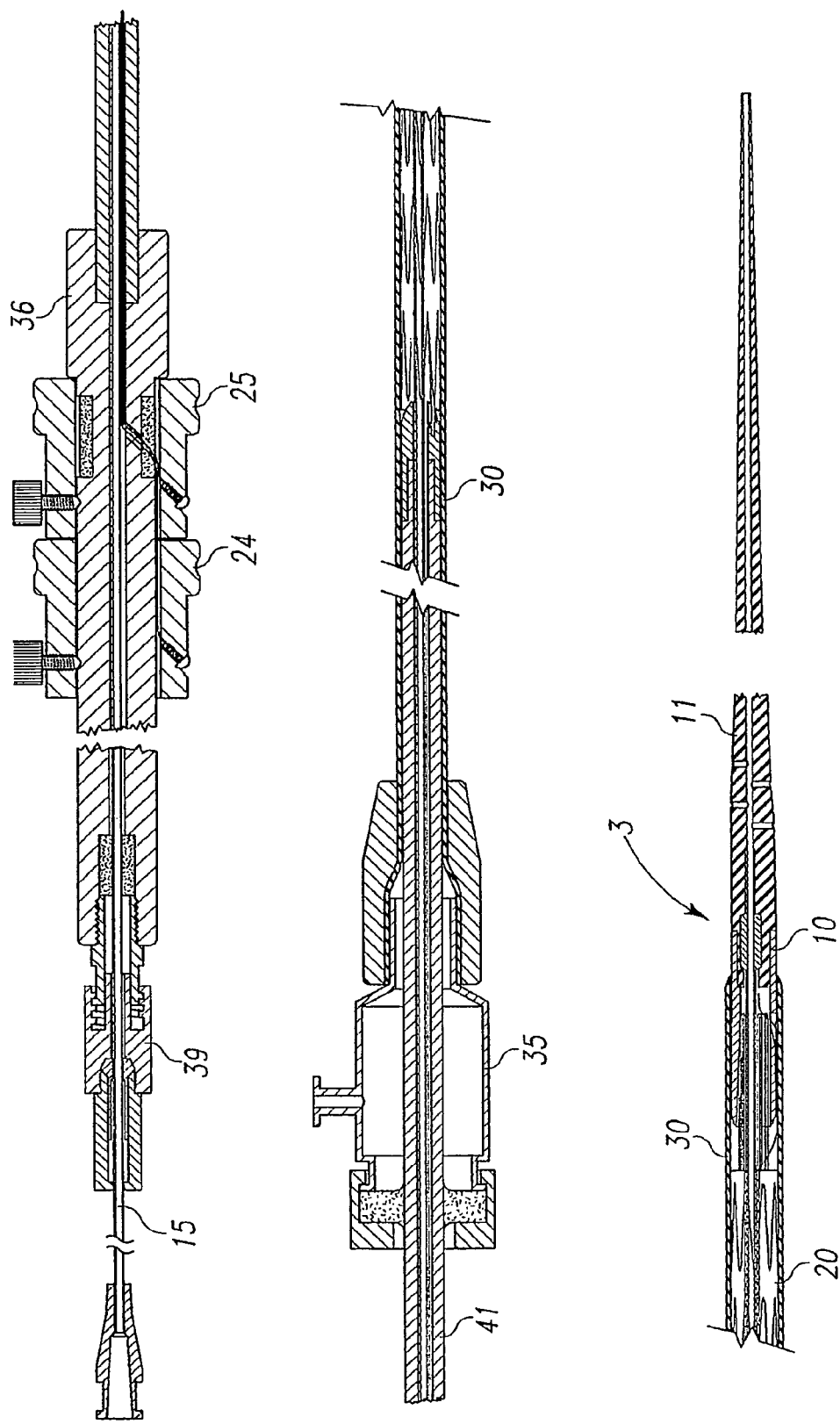
FIG. 7 is a segmented sectional view of the introducer of FIG. 1A fully loaded and ready for introduction into a patient.

In FIG. 7, the introducer assembly is shown fully assembled ready for introduction into a patient. The prosthesis 20 is retained at each of its ends by the proximal and distal retaining assemblies respectively, and compressed by the external sleeve 30. If an aortic aneurysm is to be grafted, the introducer assembly can be inserted through a femoral artery over the guide wire 13 in the form as shown in FIG. 7, and positioned by radiographic techniques (not discussed here). The fenestration 17 of the prosthesis 20 can be aligned with a branch vessel, such as a renal artery, during this positioning.

Figure 8:
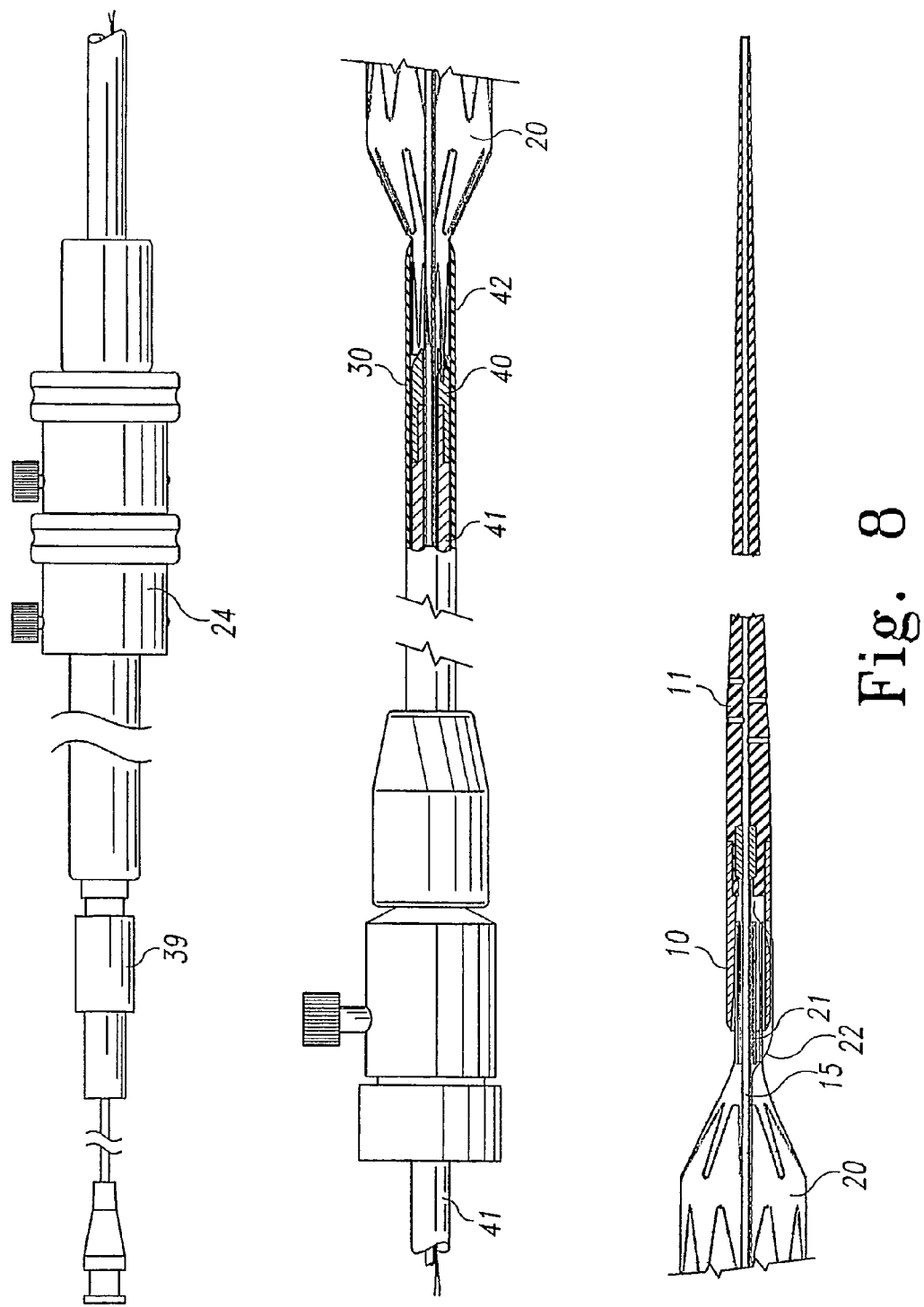
FIG. 8 is a segmented view partially in section of the introducer of FIG. 7 in the next stage of deployment of the prosthesis.

In FIG. 8, the introducer assembly is in a desired position for deployment of the prosthesis 20. The external sheath 30 is withdrawn to just proximal of the distal attachment section 40. This action releases the middle portion of the prosthesis 20 so that self-expanding zigzag stent 19 can expand radially. The proximal self-expanding stent 21, however, is still retained within the retention device 10. Also, the distal end 42 of the prosthesis 20 is still retained within the external sheath 30.

By release of the pin vise 39 to allow small movements of the thin walled tubing 15 with respect to the thick walled tubing 41, the prosthesis 20 can be lengthened or shortened or rotated or compressed for accurate placement in the desired location within the lumen. X-ray opaque markers (not shown) can be placed along the prosthesis 20 to assist with placement of the prosthesis.

Figure 9:
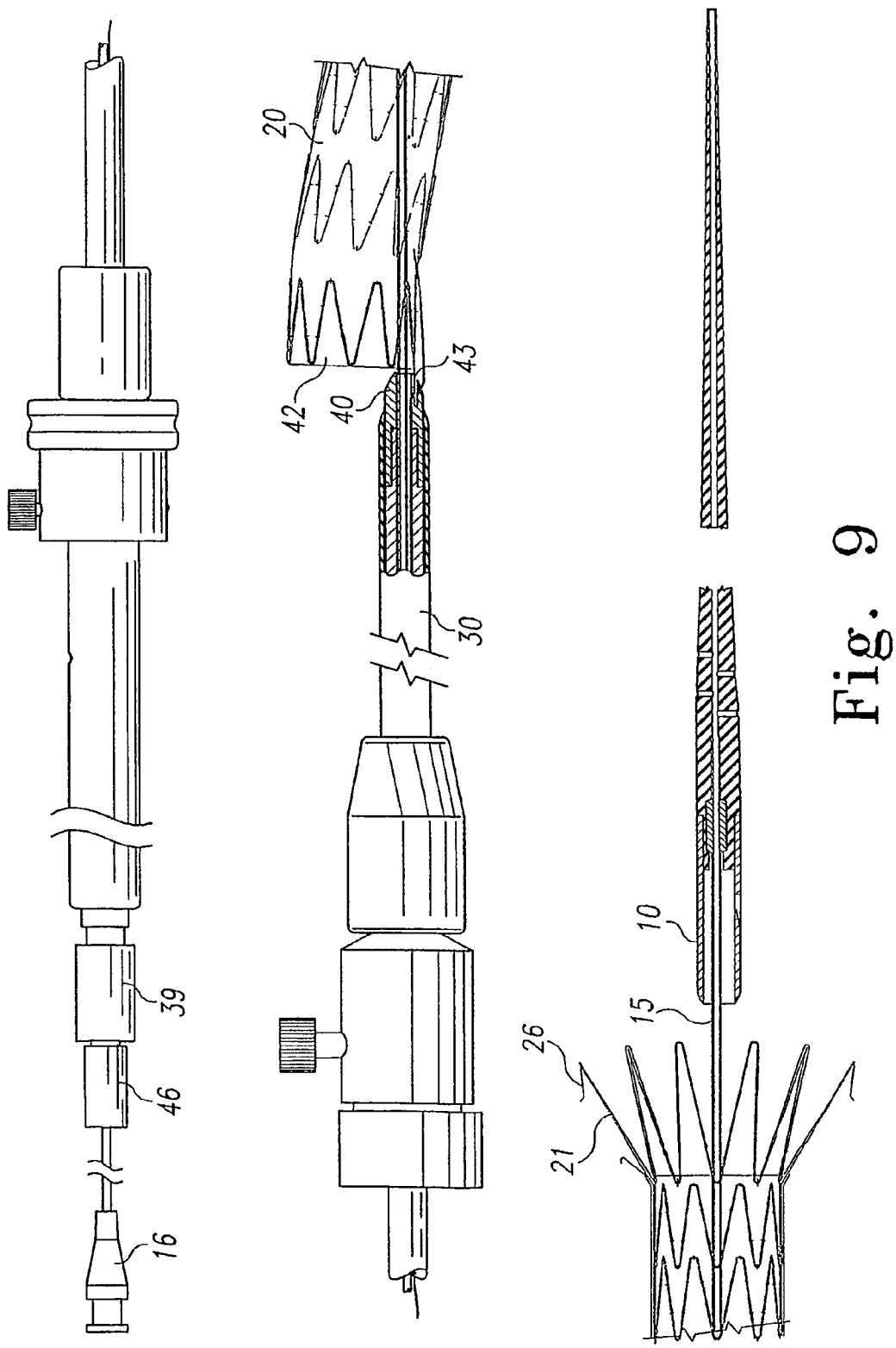
FIG. 9 is a segmented view partially in section similar to FIG. 8 of the introducer at the release of the proximal end stage of deployment.

In FIG. 9, the proximal trigger wire 22 has been removed, allowing the retention device 10 to be separated from the self-expanding zigzag stent 21, as explained above. At this stage, the proximal trigger wire release mechanism 24 and the proximal trigger wire 22 can be removed completely.

Also, the screw cap 46 of the pin vise 39 has been loosened so that the thin walled tubing 15 can been pushed in a proximal direction to move the proximal attachment means 10 in a proximal direction. When the proximal attachment means 10 no longer surrounds the self-expanding stent 21 at the proximal end of the prosthesis 20, the self-expanding stent 21 expands. When the self-expanding stent 21 expands, the hooks or barbs 26 on the self-expanding stent 21 grip into the walls of the lumen to hold the proximal end of the prosthesis 20 in place.

At this point, the distal end 42 of the prosthesis 20 is still retained by the distal attachment means 40, with the loop 43 retained therein. The external sheath 30 is then withdrawn to distal of the distal attachment section 40 to allow the distal end 42 of the prosthesis 20 to expand.

At this point, the distal end 42 of the prosthesis 20 can still be moved. Consequently, the prosthesis 20 can still be rotated or lengthened or shortened or otherwise moved for accurate positioning. Where the prosthesis 20 to be deployed is a bifurcated graft, the movement at this stage may ensure that the shorter leg is directed in the direction of the contra-iliac artery.

Figure 10:
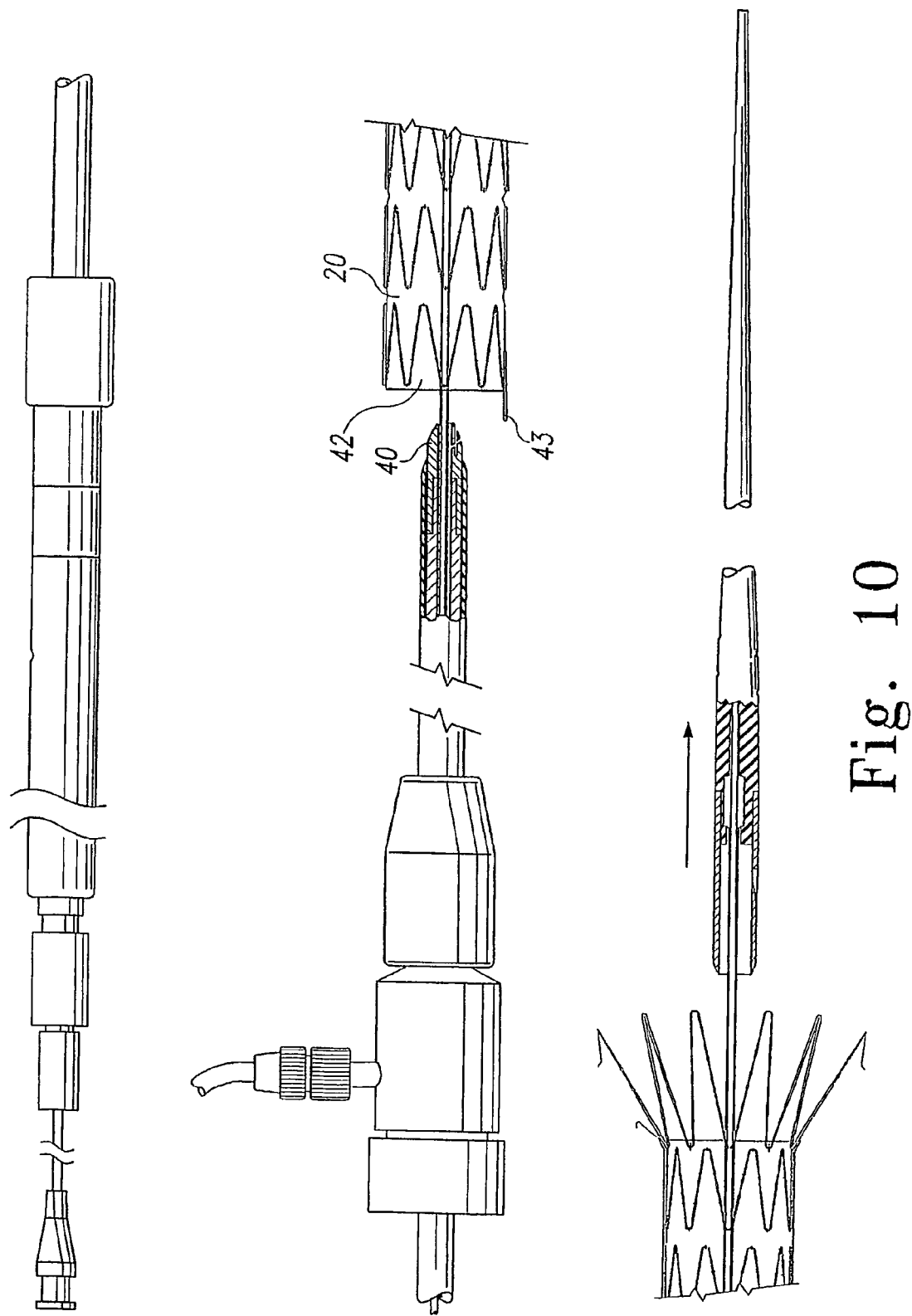
FIG. 10 is a segmented view partially in section similar to FIG. 8 of the introducer at the release of the distal end stage of deployment.

In FIG. 10, the distal end 42 of the prosthesis 20 has been released by removal of the distal trigger wire 44. At this stage, the distal trigger wire release mechanism 25 and the distal trigger wire 44 can be removed completely. This removal can be accomplished by passing the distal wire release mechanism 25 over the pin vise 39 and the connection means 16. The loop 43 of the terminal distal self-expanding zigzag stent 19 is hence released, and the prosthesis 20 is now free to expand to the walls of the vessel. At this point, the introducer is ready to be removed.

Figure 11:
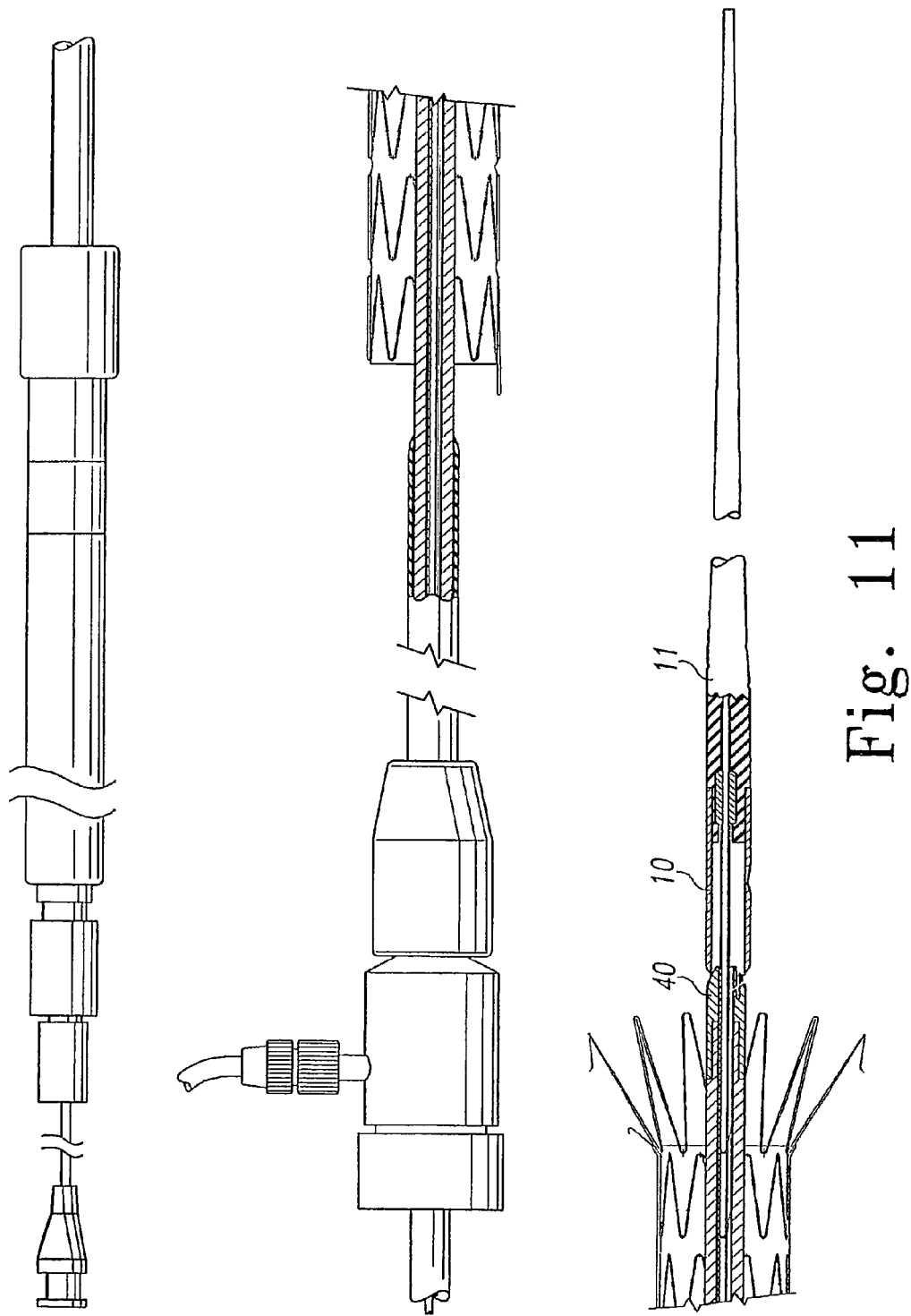
FIG. 11 is a segmented view partially in section similar to FIG. 8 illustrating the advancement of the distal attachment mechanism to the proximal attachment mechanism.

In FIG. 11, the first stage of removal is shown. First, the distal attachment section 40 is advanced until it is received in the rear of the proximal attachment device 10. Next, the proximal attachment device 10, the tapered flexible extension 11, and the distal attachment device 40 are removed together, as shown in FIG. 11.

Figure 12:
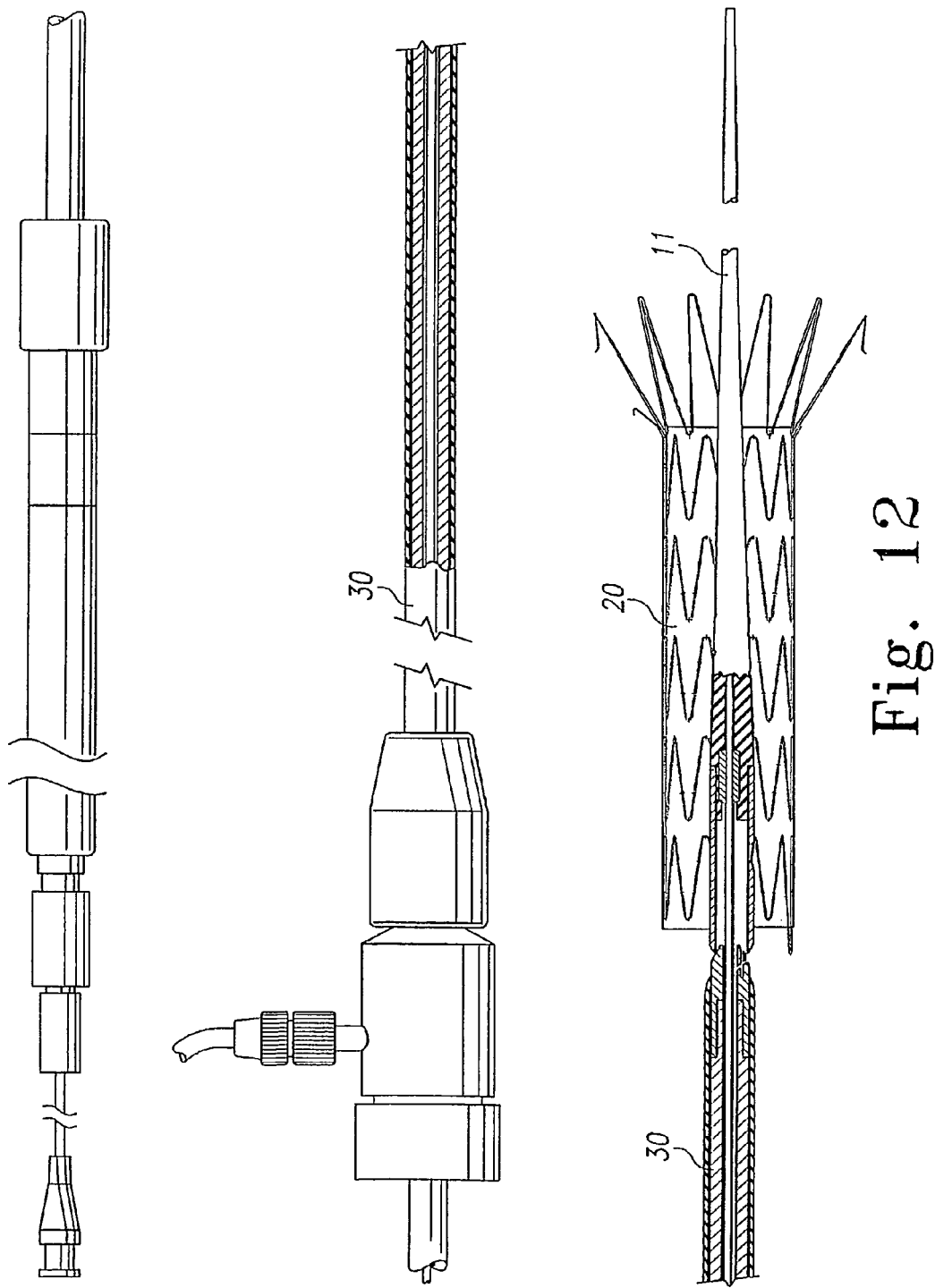
FIG. 12 is a segmented view partially in section similar to FIG. 8 of the withdrawal of the introducer.

In FIG. 12, the sheath 30 has been advanced to uncover the joint between the proximal attachment device 10 and the distal attachment section 40. The sheath 30 can be removed with the proximal attachment device 10, the tapered flexible extension 11 and the distal attachment device 40. Alternatively, these items could be removed separately, followed by removal of the external sleeve 30.

Figure 13:
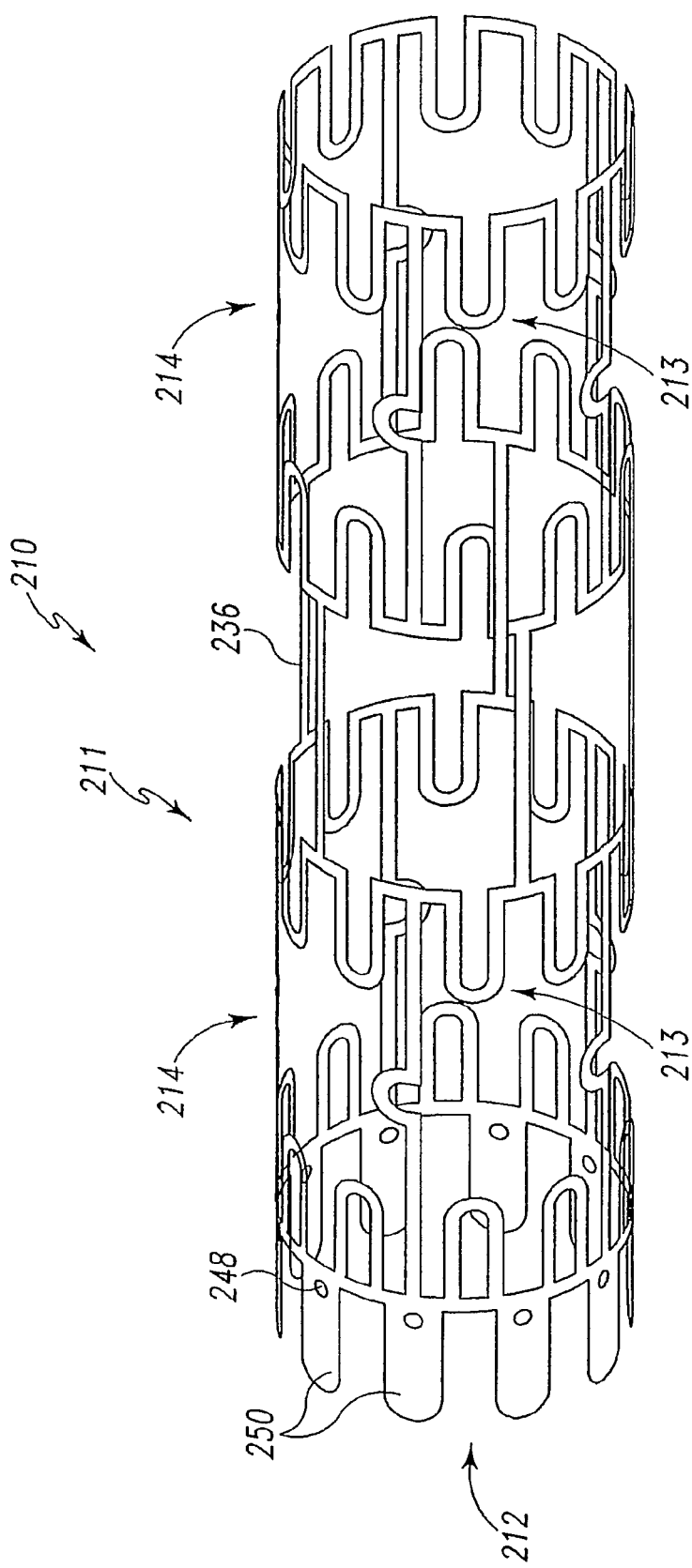
FIG. 13 is a perspective view of an expandable stent that is a radially expandable and laterally flexible.
Figure 22:
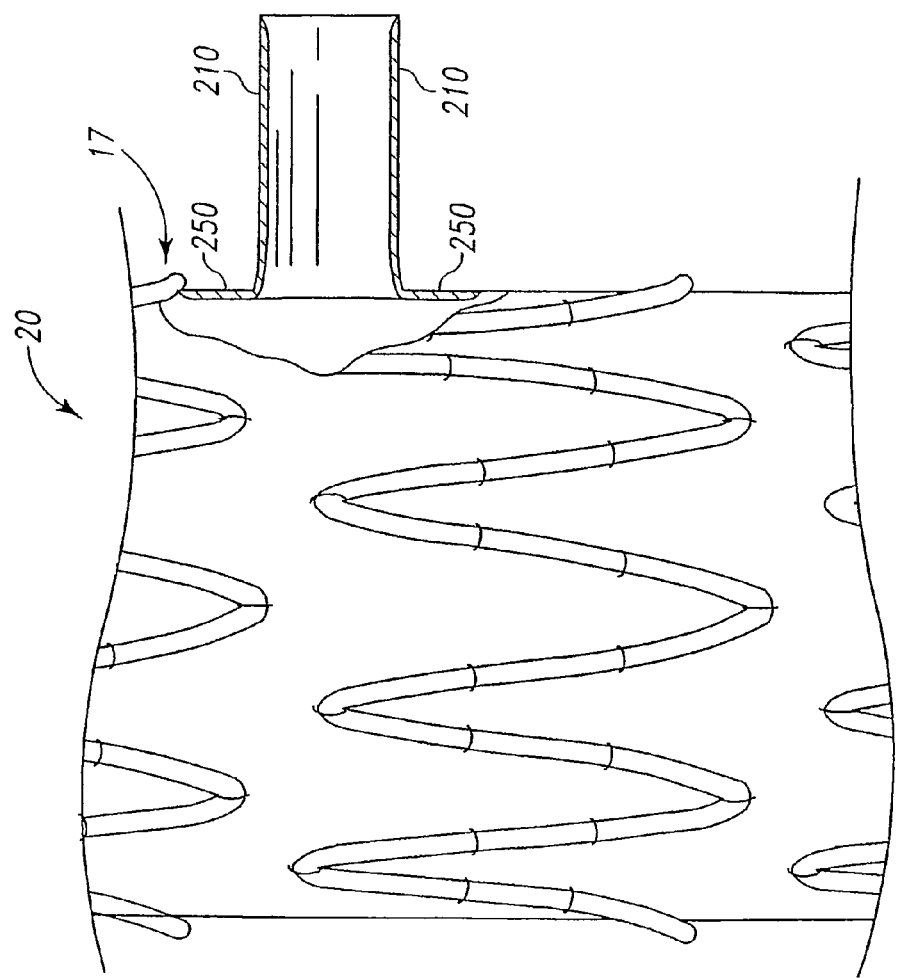
FIG. 22 is a detailed cut-away front view of the prosthesis of FIG. 1 with the stent of FIG. 13 coupled thereto.

FIG. 13 depicts an expandable stent 210, which is a radially expandable and laterally flexible. The expandable stent 210 is shown in FIG. 13 in an unexpanded state. The expandable stent 210 is configured to have an expanded outer diameter approximately equal to the diameter of fenestration 17 of the prosthesis 20, so that the expandable stent 210 can be tightly coupled to the prosthesis 20, as shown in FIG. 22.

The expandable stent 210, which is comprised of an elongated member 211 with a passage 212 extending longitudinally therethrough, is formed from a tube of malleable, biocompatible material such as stainless steel. By annealing the stainless steel, the metal is soft and plastically deformable to allow the stent 210 to be readily radially expanded using a balloon catheter, shown in FIG. 14. The endoluminal expandable stent 210 can be similar in construction to stents disclosed in U.S. Pat. No. 6,464,720 entitled "Radially Expandable Stent", which is herein incorporated by reference.

The expandable stent 210 can include a repeating series of first and second alternating segment types. The first segment type is a longitudinal segment 214 having a plurality of laterally interconnected closed cells 213. The second segment type is a flexible interconnection segment 221 that interconnects adjacent longitudinal segments via at least one interconnection strut, member, or tab 236. The longitudinal segments 214, when expanded, provide the expandable stent 210 with the radial strength required to maintain patency of a lumen or vessel such as a vein, an artery, or a duct. The interconnection segments 221 provide the expandable stent 210 with lateral flexibility necessary for placement through or into tortuous vessels or sites that are subject to many bending cycles over a large range of angles.

To form the alternating longitudinal segments 214 and 221 from a metal tube or sheet, material must be removed in some manner, such as by a commercially available computer-controlled laser, leaving a framework of integrated support members that has a small surface area relative to the initial surface area of the tube or sheet. Other methods of manufacture include chemical etching using photoresistive masking techniques, machining, electrode discharge machining (EDM), or cutting with a water jet.

Figure 24:
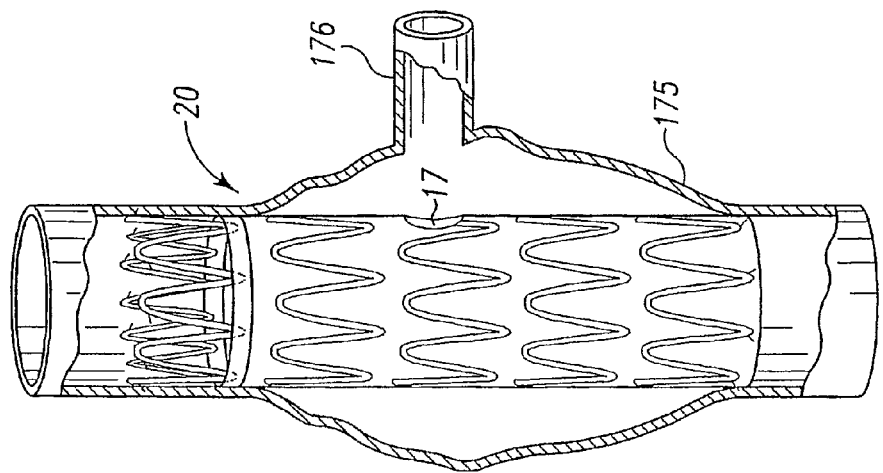
FIG. 24 is a sectional view of the main lumen and the branch lumen of FIG. 23 after the prosthesis of FIG. 1 has been implanted.

The expandable stent 210 also includes tabs 250 at an end thereof. The tabs 250 can be bent radially outward from the elongated member 211 to secure the expandable stent 210 to the prosthesis 20, as shown in FIGS. 22 and 24. The expandable stent 210 preferably includes at least one radio opaque marker 248, which is preferably positioned near the tabs 250.

Figure 14:
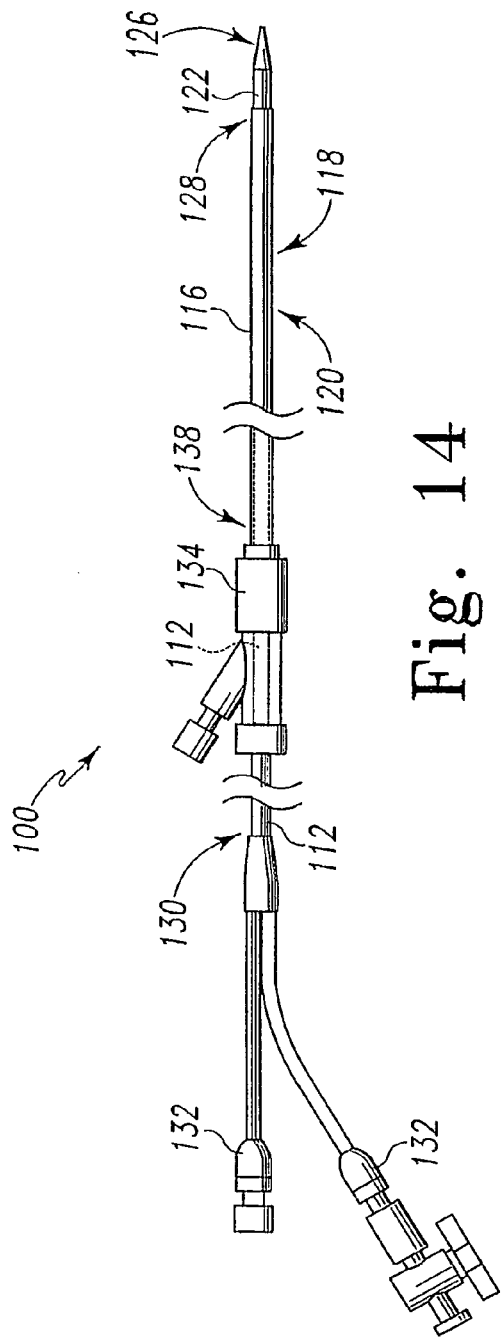
FIG. 14 is a segmented view of an endovascular introducer for deploying the expandable stent of FIG. 13.

FIG. 14 shows and an endovascular introducer 100 for deploying the expandable stent 210. The introducer 100 can be similar to the introducers disclosed in U.S. Pat. No. 6,447,540 entitled "Stent Deployment Device Including Splittable Sleeve Containing the Stent", which is herein incorporated by reference. The introducer 100 can comprise a catheter 112, the expandable stent 210 positioned on the catheter 112, and a sleeve 116 carried on the catheter 112. The introducer 100 can further comprise a mechanism 120 for inflating a first balloon 122 and a second balloon 123 (see FIG. 15) to expand the expandable stent 210. The sleeve 116 can be retractable to expose the expandable stent 210, as shown in FIG. 16.

One or more fluid couplings 132 are provided at the proximal end 130 of the catheter 112, through which a pressurized fluid is supplied to the first balloon 122 and the second balloon 123 through lumens for inflation. The sleeve 116 can be substantially the same length as the catheter 112 and include a proximal end 138 slidably coupled to the catheter 112, for example, near the proximal end 130 of the catheter 112 at the coupling 134. The sleeve 116 can be composed of any of a variety of materials, some more suited to particular applications than others. The sleeve 116 can be composed of an indistensable material. The sleeve 116 can also be composed of a medical grade material, which can be either physiologically inert or biodegradable.

Figure 15:
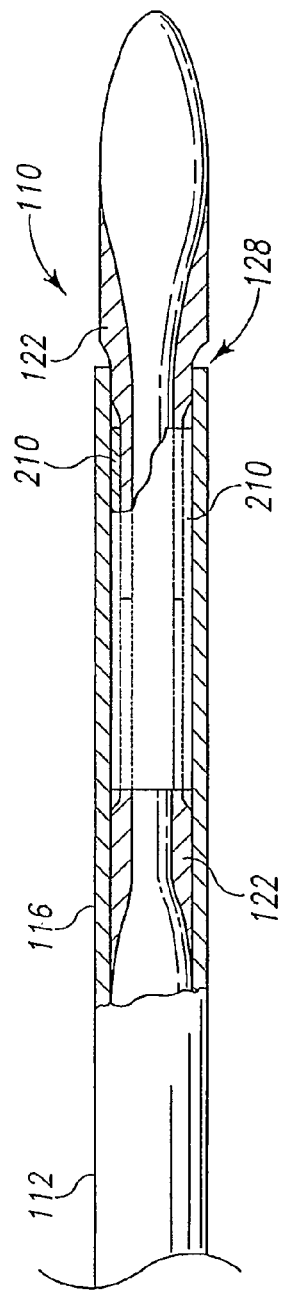
FIG. 15 is a detailed cut-away view of a portion of the endovascular introducer of FIG. 14.

FIG. 15 is a detailed cut-away view of a distal portion 110 of the endovascular introducer 100. Prior to insertion into a patient, the sleeve 116 covers the expandable stent 210. The first balloon 122 and the second balloon 123 are deflated during insertion. The expandable stent 210 and the portion of the sleeve 116 extending over the stent 210 and thus positioned over the first balloon 122, with the distal end 128 of the sleeve 116 lying just distally of the expandable stent 210. The first balloon 122 and the second balloon 123 are carried on the catheter 112 near the distal tip 110 of the catheter 112. Although not depicted, a first lumen extends longitudinally through the catheter 112 between the first balloon 122 and one of the proximal couplings 132. Likewise, a second lumen extends longitudinally through the catheter 112 between the second balloon 123 and another of the proximal couplings 132.

FIG. 16 is a detailed cut-away view of a distal portion 110 of the endovascular introducer 100 with the sleeve 116 slid back to expose the expandable stent 210. The first balloon 122 and the second balloon 123 can be clearly seen. FIG. 17 is a detailed cross-sectional view of the distal portion 110 of the endovascular introducer 100 where the expandable stent 210 is shown sectioned to reveal the first and second balloons 122 and 123. The balloons 122 and 123 can have different compliances.

For example, the first balloon 122 can comprise a material that is compliant, while the second balloon 123 can comprise a material that is semi-compliant or noncompliant. Alternatively, the both the first and second balloons 122 and 123 can comprise a semi-compliant or noncompliant material, in which case the balloons 122 and 123 can have different diameters. As used herein, the terms "compliant", "semi-compliant", and "non-compliant" have the same meanings as defined in U.S. Pat. No. 5,556,383 entitled "Block Copolymer Elastomer Catheter Balloons", which is herein incorporated by reference.

Figure 18:
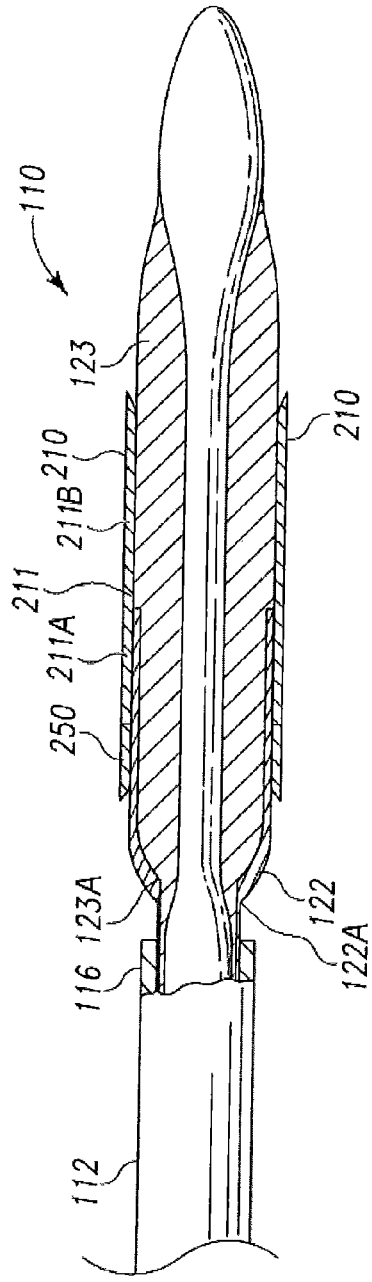
FIG. 18 is a detailed cross-sectional view similar to FIG. 17 with a first balloon expanded.

In operation, the second balloon 123 is inflated to a first diameter, as shown in FIG. 18. This diameter will be substantially equal to the diameter of a fenestrated artery (branch lumen) in which the expandable stent 210 is to be placed. Inflation of the second balloon 123 can be accomplished with fluids introduced through one of the proximal couplings 132. The second balloon 123 can be inflated until the expandable stent 210 is expanded to the first diameter, as shown. As shown in FIG. 18, the tabs 250 of the expandable stent 210 overlie the first balloon 122 to be in contact against the first balloon. As shown in FIG. 18, the elongated member 211 of the expandable stent 210 overlies the first balloon 122 to be in contact against the first balloon and overlies the second balloon 123 to be in contact against the second balloon. In other words, the elongated member 211 has a first portion 211A adjacent the tabs 250 that contacts the distal end of the first balloon 122 and a second portion 211B adjacent the first portion 211A that contacts the proximal portion of the second balloon 123. As shown in FIG. 18, the tabs 250 of the expandable stent 210 and the elongated member 211 expand to the first diameter upon expansion of the second balloon 123 within the first balloon 122. A proximal end 122A of the first balloon 122 and a proximal end 123A of the second balloon 123 extend proximally beyond the end of the tabs 250 of the expandable stent 210, as shown in FIG. 18.

Figure 19:
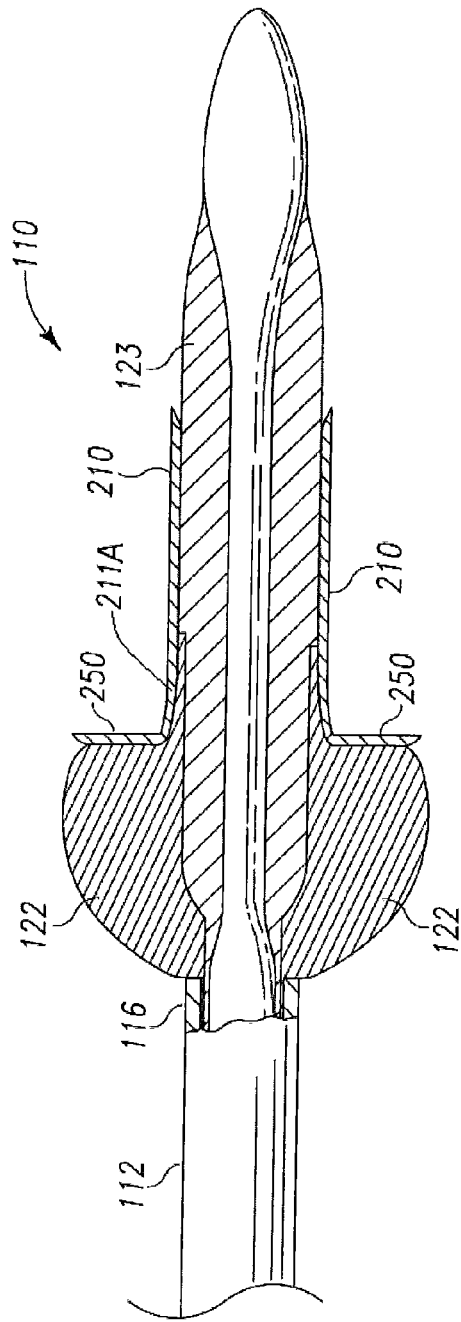
FIG. 19 is a detailed cross-sectional view similar to FIG. 17 with a second balloon expanded.

As shown in FIG. 19, the first balloon 122 is inflated to a second diameter that is substantially greater than the diameter of the fenestrated artery (branch lumen) in which the expandable stent 210 is to be placed. Inflation of the first balloon 122 can also be accomplished with fluids introduced through another of the proximal couplings 132. The first balloon 122 can be inflated until the tabs 250 of the expandable stent 210 are "bent back" to about a ninety degree angle from the elongated member 211, as shown. As shown in FIG. 19, the tabs 250 are moved to a flared shape upon expansion of the first balloon 122 to the second diameter. As shown in FIG. 19, the first portion 211A of the elongated portion of the expandable stent 210 is slightly expanded or tapered relative to the remaining elongated portion upon expansion of the first balloon 122.

Although not shown, in another preferred embodiment, the first balloon 122 extends over the second balloon 123 to the distal tip 110 of the catheter 112. In this preferred embodiment, the second balloon 123 comprises a semi-compliant or noncompliant material, while the first balloon 122 comprises a compliant material. In operation, the second balloon 123 is inflated to a first diameter that is substantially equal to the diameter of the fenestrated artery, while the first balloon 122 is inflated to a second diameter that is substantially greater than the first diameter. In substantially the same manner as above, the second balloon 123 expands the expandable stent 210, and the first balloon 122 "bends back" the tabs 250 of the expandable stent 210.

In yet another preferred embodiment (not shown), the first balloon 122 and the second balloon 123 are separate sections of a "single" balloon. Again, the first balloon 122 and the second balloon 123 can comprise a semi-compliant or noncompliant material and be of different diameters, or the first balloon 122 can comprise a compliant material while the second balloon 123 can comprise a semi-compliant or noncompliant material. Essentially, in each preferred embodiment, one or more balloons are provided to inflate to two or more diameters, where one diameter is sufficient to expand the expandable stent 210, while a second diameter is sufficient to "bends back" the tabs 250 of the expandable stent 210, or, if the expandable stent 210 has no tabs, sufficient to flair one end of the expandable stent 210.

Figure 20:
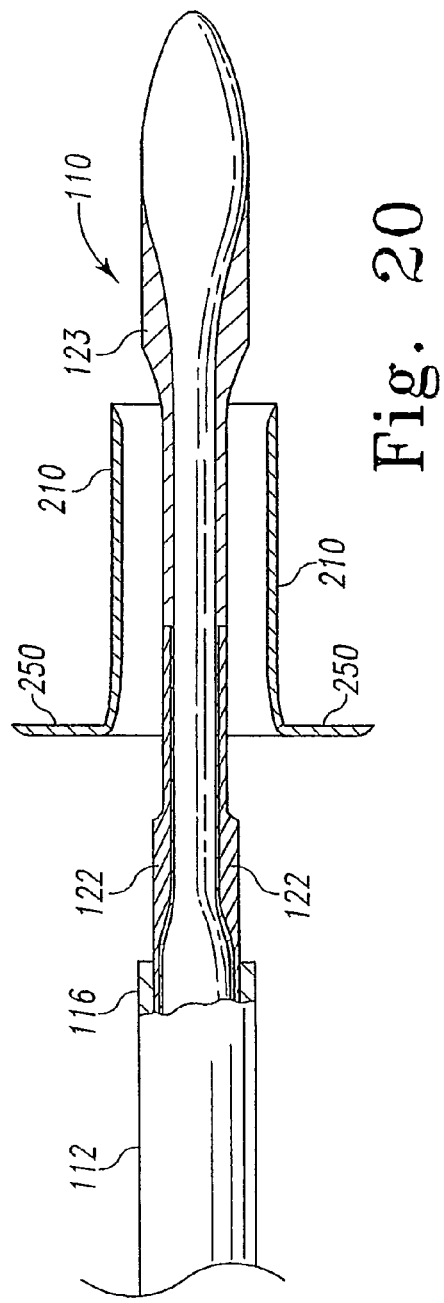
FIG. 20 is a detailed cross-sectional view similar to FIG. 19 with the first and second balloon collapsed.
Figure 21:
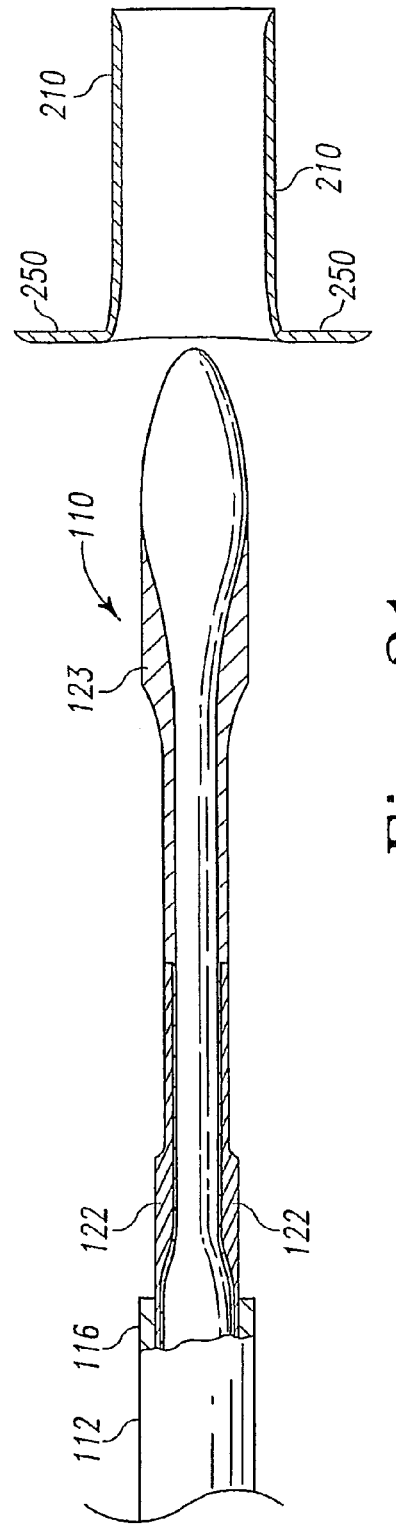
FIG. 21 is a detailed cross-sectional view of a portion of the endovascular introducer shown in FIG. 14 being removed from the stent.

FIG. 20 is a detailed cut-away view of a distal portion 110 of the endovascular introducer 100 with the first balloon 122 and the second balloon 123 collapsed. The expandable stent 210 retains the expanded diameter formed by the first balloon 122. Likewise, the tabs 250 of the expandable stent 210 retain the flared shape formed by the inflation of the second balloon 123. FIG. 21 shows the endovascular introducer 100 being withdrawn from the expandable stent 210.

FIG. 22 is a detailed cut-away view of the prosthesis 20, and a cross-sectional view of the expandable stent 210. The expandable stent 210 is shown in located in the fenestration 17 of the prosthesis 20, and the tabs 250 anchor the expandable stent 210 to the prosthesis 20.

Figure 25:
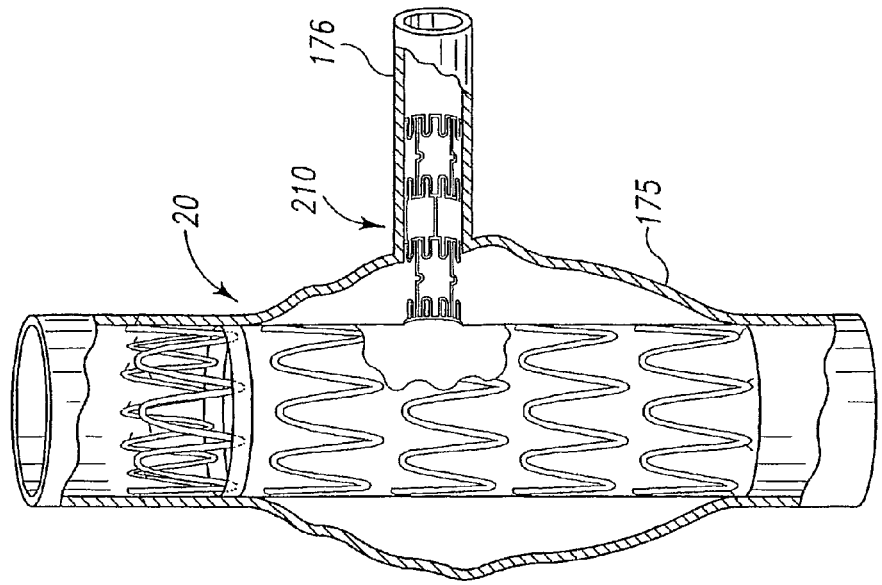
FIG. 25 is a sectional view of the main lumen and the branch lumen of FIG. 23 after both the prosthesis of FIG. 1 and the stent of FIG. 13 have been implanted.
Figure 23:
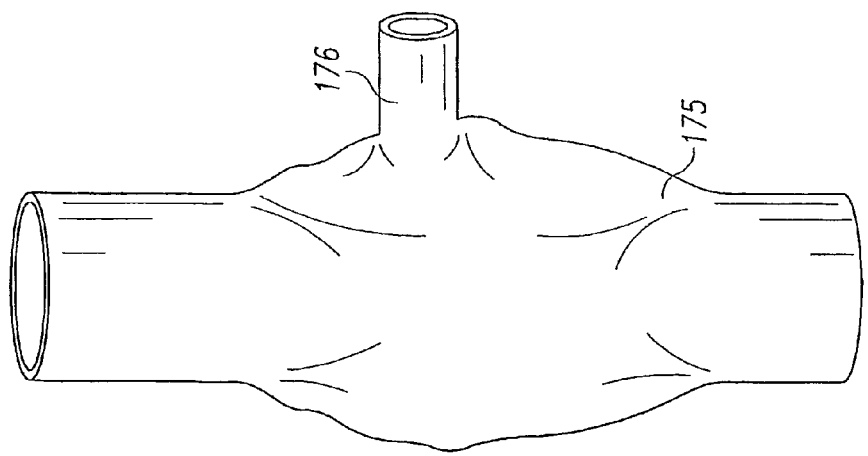
FIG. 23 is an elevation view of a main lumen and a branch lumen fluid communication with the main lumen.

FIG. 23 is a front view of a main lumen 175 and a branch lumen 176, wherein the lumens 175 and 176 are in fluid communication. The main lumen 175 has an aneurysm, or weakness, and exists at the attachment point of the branch lumen 176. FIG. 24 shows the lumens 175 and 176 after the prosthesis 20 has been successfully implanted. The fenestration 17 is aligned with the opening of the branch lumen 176. The prosthesis 20 reinforces the main lumen 175. FIG. 25 shows the lumens 175 and 176 after the expandable stent 210 has been successfully implanted. The expandable stent 210 performs two main functions. First, the expandable stent 210 keeps the fenestration 17 aligned so that the lumens 175 and 176 remain in fluid communication. Second, the expandable stent 210 reinforces the branch lumen 176, which may also be weakened because of the aneurysm.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but can reside in two or more of these combined together. Accordingly, the invention is not to be restricted except in light of the attached claims and their equivalents.

The invention claimed is:

1. A stent deployment device for deploying a branch vessel stent in a branch vessel branching from a main vessel, comprising:
 a catheter, a first balloon, a second balloon positioned near a distal end of the catheter and expandable to a first diameter, the first balloon disposed proximal to and extending coaxially only partially over a proximal end of the second balloon, the first balloon being expandable to a second diameter that is larger than the first diameter, and an expandable stent positioned over the first balloon and over the second balloon, the expandable stent having a flareable end portion configured to reside in the main vessel and a tubular portion configured to reside in the branch vessel and coupled to the flareable end portion, the flareable end portion overlying the first balloon, the tubular portion overlying at least the second balloon, where expansion of the first balloon expands the flareable end portion of the stent to at least the second diameter, and expansion of the second balloon expands the tubular portion of the stent to the first diameter, wherein the first balloon comprises a more compliant material than the second balloon.

2. A stent deployment device for deploying a branch vessel stent in a branch vessel branching from a main vessel, comprising:
 a catheter, a first balloon, a second balloon positioned near a distal end of the catheter and expandable to a first diameter, the first balloon positioned proximal to and coaxially over a proximal end of the second balloon so that a distal portion of the second balloon extends longitudinally beyond the first balloon, and expandable to a second diameter greater than the first diameter, and
 an expandable stent comprising a tubular elongated body portion configured to reside in the branch vessel and a flareable proximal portion extending proximally from the elongated body portion and configured to reside in the main vessel, the expandable stent positioned coaxially over the first and second balloons, the flareable proximal portion overlying the first balloon and the elongated body portion overlying and at least a proximal portion of the second balloon,
 wherein both of the flareable proximal portion and the elongated body portion are configured to expand to the first diameter upon expansion of the second balloon within the first balloon, and the flareable proximal portion is configured to move to a flared shape upon expansion of the first balloon to the second diameter.

3. The device of claim 2 wherein the first balloon comprises a more compliant material than the second balloon.

4. The device of claim 1 wherein the first balloon comprises a semi-compliant material.

5. The device of claim 1 wherein the first balloon comprises a noncompliant material.

6. The device of claim 1 wherein the first balloon comprises a compliant material.

7. The device of claim 1 wherein the second balloon comprises a semi-compliant material.

8. The device of claim 1 wherein the second balloon comprises a noncompliant material.

9. The device of claim 1 wherein the second balloon comprises a compliant material.

10. The device of claim 1 wherein the expandable stent comprises an elongated body with a passage extending longitudinally therethrough.

11. The device of claim 10 wherein the expandable stent comprises a plurality of bendable tabs located at said first portion of the expandable stent.

12. The device of claim 11 wherein the plurality of bendable tabs are positioned coaxially over the first balloon.

13. The device of claim 11 wherein each of the bendable tabs are configured to bend substantially radially outwardly from the body of the expandable stent when a force is applied to the bendable tabs from an inside of the body of the expandable stent.

14. The device of claim 11 wherein the expandable stent comprises a radio opaque marker positioned on the body of the expandable stent near one of the bendable tabs.

15. The device of claim 10 wherein the expandable stent comprises a radio opaque marker coupled to the body of the expandable stent.

16. The device of claim 1 wherein said second diameter is at least twenty-five percent greater than said first diameter.

17. The device of claim 16 wherein the second diameter is at least fifty percent greater than the first diameter.

18. The device of claim 17 wherein the second diameter is at least twice the first diameter.

19. A stent deployment device for deploying a branch vessel stent in a branch vessel branching from a main vessel, comprising:

a catheter, a first balloon comprising a compliant material, a second balloon comprising a non-compliant or semi-compliant material, positioned near a distal end of the catheter and expandable to a first diameter, the first balloon positioned proximal to and extending over at least a proximal end of the second balloon to define a coaxial, overlapping portion, the first balloon expandable to a second diameter greater than the first diameter, and an expandable stent comprising a flareable proximal end located at a longitudinal end thereof and configured to lie in the main vessel, the expandable stent positioned partially over the first balloon and partially over the second balloon, the flareable end positioned coaxially over the first balloon, wherein the entire expandable stent is configured to expand to the first diameter upon expansion of the second balloon, and the flareable proximal end of the expandable stent is configured to bend substantially radially outward from a body of the expandable stent when a force is applied to the flareable proximal end upon expansion of the first balloon and to expand within the main vessel.

20. The device of claim 19 wherein a proximal end of each of the first and second balloons extend proximally beyond the flareable proximal end of the expandable stent.

* * * * *